United States Patent
Borsic

(10) Patent No.: US 12,262,935 B2
(45) Date of Patent: Apr. 1, 2025

(54) SYSTEM AND METHODS FOR ABLATION TREATMENT OF TISSUE

(71) Applicant: NE Scientific, LLC, Boston, MA (US)

(72) Inventor: Andrea Borsic, Turin (IT)

(73) Assignee: NE Scientific, LLC, Boston, MA (US)

( * ) Notice: Subject to any disclaimer, the term of this patent is extended or adjusted under 35 U.S.C. 154(b) by 0 days.

(21) Appl. No.: 17/890,839

(22) Filed: Aug. 18, 2022

(65) Prior Publication Data

US 2023/0263565 A1 Aug. 24, 2023

Related U.S. Application Data

(63) Continuation of application No. 15/427,884, filed on Feb. 8, 2017, now Pat. No. 11,419,660.

(Continued)

(51) Int. Cl.
*A61B 18/12* (2006.01)
*A61B 18/14* (2006.01)
(Continued)

(52) U.S. Cl.
CPC ...... *A61B 18/1206* (2013.01); *A61B 18/1815* (2013.01); *A61B 34/25* (2016.02); *A61B 90/37* (2016.02); *A61B 2018/00577* (2013.01); *A61B 2018/00613* (2013.01); *A61B 2018/00785* (2013.01); *A61B 2018/00791* (2013.01); *A61B 2018/00875* (2013.01);
(Continued)

(58) Field of Classification Search
CPC . A61B 18/1206; A61B 34/25; A61B 18/1815; A61B 2034/301; A61B 34/20; A61B 2034/2046; A61B 2034/104; A61B 2034/107; A61B 18/1482; A61B 90/37; A61B 2018/00577; A61B 2018/00613; A61B 2018/00785; A61B 2018/00791; A61B 2018/00875; A61B 2018/1253; A61B 2018/1432; A61B 2018/1467; A61B 2018/1861; A61B 2090/378; A61B 2090/3762
USPC .......................................................... 606/21
See application file for complete search history.

(56) References Cited

U.S. PATENT DOCUMENTS 6,484,118 B1 * 11/2002 Govari .................. A61B 34/20
702/94
7,452,357 B2 11/2008 Vlegele et al.
(Continued)

FOREIGN PATENT DOCUMENTS

JP 2001500762 A * 1/2001

*Primary Examiner* — Joshua E Rodden
(74) *Attorney, Agent, or Firm* — Pandiscio & Pandiscio

(57) ABSTRACT

A system for ablation treatment of tissues including at least one tissue ablation device, an ablation device controller communicatively connected to the at least one tissue ablation device, and an imaging component, wherein the imaging component is configured to capture a captured image that includes a representation of the tissue ablation device. The system further including an ablation device identification component configured to receive the captured image, generate a plurality of region proposals from the captured image, extract a plurality of feature vectors from the plurality of region proposals, determine a class for each region proposal of the plurality of region proposals, and determine the position and orientation of the tissue ablation device as a function of the classes for each region proposal.

14 Claims, 26 Drawing Sheets

Related U.S. Application Data

(60) Provisional application No. 62/293,102, filed on Feb. 9, 2016.

(51) Int. Cl.
- *A61B 18/18* (2006.01)
- *A61B 34/00* (2016.01)
- *A61B 34/20* (2016.01)
- *A61B 90/00* (2016.01)
- *A61B 18/00* (2006.01)

(52) U.S. Cl.
CPC ............... *A61B 2018/1253* (2013.01); *A61B 2018/1432* (2013.01); *A61B 2018/1467* (2013.01); *A61B 18/1482* (2013.01); *A61B 2018/1861* (2013.01); *A61B 2034/2065* (2016.02); *A61B 2090/374* (2016.02); *A61B 2090/3762* (2016.02); *A61B 2090/378* (2016.02)

(56) References Cited

U.S. PATENT DOCUMENTS

| | | | | |
|---|---|---|---|---|
| 7,670,291 | B2* | 3/2010 | Vaezy | A61B 8/12 600/443 |
| 8,187,260 | B1* | 5/2012 | Bao | A61B 8/4263 606/23 |
| 9,901,406 | B2* | 2/2018 | State | G06T 19/00 |
| 10,828,105 | B2* | 11/2020 | Sahay | A61B 6/5235 |
| 11,931,117 | B2* | 3/2024 | Heaney | A61B 34/25 |
| 2001/0047133 | A1* | 11/2001 | Gilboa | A61B 5/062 600/429 |
| 2002/0049375 | A1* | 4/2002 | Strommer | A61B 8/0841 600/407 |
| 2003/0013958 | A1* | 1/2003 | Govari | A61B 8/483 600/443 |
| 2006/0155267 | A1* | 7/2006 | Berzak | A61B 18/02 606/20 |
| 2007/0135712 | A1* | 6/2007 | Maschke | A61F 2/95 600/433 |
| 2008/0033417 | A1* | 2/2008 | Nields | A61B 18/1815 606/41 |
| 2008/0312673 | A1* | 12/2008 | Viswanathan | A61B 90/36 606/159 |
| 2009/0171203 | A1 | 7/2009 | Avital et al. | |
| 2010/0152590 | A1* | 6/2010 | Moore | A61B 8/4461 600/466 |
| 2010/0161023 | A1* | 6/2010 | Cohen | A61B 17/1204 623/2.11 |
| 2011/0082351 | A1* | 4/2011 | Razzaque | A61B 5/744 600/301 |
| 2011/0251607 | A1* | 10/2011 | Kruecker | A61B 18/1815 600/407 |
| 2012/0173217 | A1 | 7/2012 | Heimbecher | |
| 2012/0277763 | A1* | 11/2012 | Greenblatt | A61B 18/12 607/101 |
| 2013/0317363 | A1* | 11/2013 | Case | A61B 8/483 600/439 |
| 2014/0058387 | A1 | 2/2014 | Kruecker et al. | |
| 2014/0343404 | A1 | 11/2014 | Razzaque et al. | |
| 2015/0057646 | A1* | 2/2015 | Aljuri | A61B 1/307 606/10 |
| 2015/0374260 | A1 | 12/2015 | Govari et al. | |
| 2017/0209218 | A1 | 7/2017 | Sahay et al. | |
| 2018/0042679 | A1 | 2/2018 | Dalal et al. | |
| 2018/0161097 | A1 | 6/2018 | Zoabi et al. | |
| 2020/0214768 | A1 | 7/2020 | Baumann et al. | |
| 2023/0263565 | A1* | 8/2023 | Borsic | A61B 34/25 703/11 |

* cited by examiner

1001

SYSTEM AND METHODS FOR ABLATION TREATMENT OF TISSUE

RELATED APPLICATIONS

This application is a continuation-in-part of Non-provisional application Ser. No. 15/427,884 filed on Feb. 8, 2017 and entitled "SYSTEM AND METHODS FOR ABLATION TREATMENT OF TISSUE," the entirety of which is incorporated herein by reference, which claims the benefit of priority of U.S. Provisional Patent Application Ser. No. 62/293,102, filed on Feb. 9, 2016, which is incorporated by reference herein in its entirety.

STATEMENT REGARDING FEDERALLY SPONSORED RESEARCH OR DEVELOPMENT

This invention was made with government support under R43 CA189515 awarded by the National Institutes of Health. The government has certain rights in the invention.

FIELD OF THE INVENTION

The present disclosure generally pertains to systems and methods for interventional guidance of tissue ablation procedures.

BACKGROUND OF THE INVENTION AND RELATED ART

Ablation technologies are used to necrotize tissues for therapeutic purposes. An example of application is treatment of cancer, where ablation is used to treat malignant tissues in order to cure or manage the disease. Another example of application is treatment of arrhythmia, where ablation is used to scar or destroy tissues in the heart that trigger or sustain abnormal heart rhythms.

Various ablation technologies exist, based on different physical principles. Radio Frequency Ablation (RFA) is based on the application of Radio Frequency (RF) energy to the tissues by means of one or multiple contacting electrodes, and on heating up tissues to a temperature high enough to cause tissue necrosis. Microwave Ablation (MWA) is based on the application of Micro Wave (MW) energy to the tissues by means of a contacting antenna, and on heating up tissues to a temperature high enough to cause tissue necrosis. Cryoablation (CRA) is based on the application of cold temperatures to the tissues, by means of a contacting device, and on cooling down tissues to temperatures that cause tissue necrosis. Irreversible Electroporation (IRE) is based on the application to tissues by contacting electrodes of short-duration high-voltage electric Direct Current (DC) pulses which result in damage to tissue cells and in tissue necrosis. Laser Ablation (LA) where laser light is diffused in the tissue heating up tissues and causing necrosis.

The above ablation techniques can be applied in minimally invasive fashion. RFA, for example, which is used for treatment of liver, lung, breast and other forms of cancer, can be performed percutaneously, with needle-shaped electrodes, which are inserted into the tissues through the skin. RFA is also used, for example, in the treatment of arrhythmia, where heart tissues causing arrhythmia are treated with a catheter carrying an RFA electrode. Similarly MWA can be performed percutaneously, for example, in the treatment of liver cancer and other forms of cancer, using needle shaped MWA antennas. MWA can also be used, for example, in the treatment of arrhythmia, reaching the target tissues with a catheter. Similarly to RFA and MWA, CRA is used percutaneously for the treatment of tumors, by inserting needle-shaped cryo-probes into the tissues, and, for example, in the treatment of heart arrhythmia, by using catheters able to cool down contacting tissues. IRE is used to percutaneously treat tumors by inserting two or more needle-shaped electrodes in the tissues and by applying electric pulses between pairs of them. LA is used percutaneously for the treatment of tumors, using a needle-shaped probe which has a laser light diffuser typically at its tip, and which permits the application of laser energy to the tissues.

In the following, the term "ablation device" is used to refer to devices able to perform the ablation of tissues, such as, but not limited to, RFA electrodes, MWA antennas, IRE needles, and CRA cryo-probes.

In the minimally invasive use of ablation technologies, the operator has no direct view of the tissues that are being treated, as the ablation device is inserted into the body, for example, percutaneously or endoscopically. These procedures are image-guided, where Computed Tomography (CT), Ultrasound (US), Magnetic Resonance Imaging (MRI), or Fluoroscopy (FL) images are acquired intraoperatively and used to visualize the tissues and the position of the device within the body.

The aim of a procedure is to treat completely the volume of target tissues (e.g. a tumor) and optionally some margins around the target, which are also considered as targets for the procedure. A procedure is adequate if all the target tissues and any defined margin are treated. Reaching adequacy might require multiple overlapping ablations in order to fully treat the volume of target tissues and margins.

In often cases, the evaluation of adequacy under image guidance is difficult, as the imaging modality might not be sensitive enough to highlight clearly all the tissues that have been treated, or because the imaging modality might require administration of contrast to the patient for the treated tissues to enhance, but the operator might be limited in the dose of contrast administered, as the contrast might be toxic.

Under image guidance it might be challenging therefore to evaluate whether adequacy has been reached. For example, local recurrence of tumors treated by ablation is largely attributed to procedures that were inadequate, but interpreted as adequate, resulting in certain malignant tissues left untreated.

Systems have been proposed to improve chances of fully treating target tissues and reaching adequacy. Many of the proposed systems integrate a treatment planning system with a navigation system. The treatment planning system allows the operator to develop an interventional plan based on a number of positions and orientations of the ablation device that will result in the complete treatment of the target tissues—through the set of treatment volumes deriving from the different positions and orientations of the device. During the execution of the plan, the navigation component will acquire the intracorporeal position and orientation of the ablation device and provide some form of feedback, usually through a Graphical User Interface (GUI), to the operator to facilitate placing the ablation device in the positions and orientations required by the treatment plan. Examples of such systems are in patents US 2011/0251607 A1, U.S. Pat. No. 7,452,357 B2, US 20130317363 A1.

Systems that include a navigation component relay usually on optical, electromagnetic, or ultrasound surgical tools tracking technologies to track the spatial position and orientation of the ablation device. These tracking systems increase the cost of the overall ablation system, introduce clutter in the operating room, in certain cases limit the movement of the operator—optical systems require the line of sight to the surgical tool to be uninterrupted—and require integration of the ablation device with the tracking technology, by securing, for example, fiducials, optical markers, or electromagnetic coils to the ablation device.

SUMMARY OF THE DISCLOSURE

In an aspect, a system for ablation treatment of tissues, the system including at least one tissue ablation device, an ablation device controller communicatively connected to the at least one tissue ablation device, wherein the ablation device controller is configured to control the ablation effect of the at least one ablation device, and an imaging component, wherein the imaging component is configured to capture a captured image, wherein the captured image includes a representation of the tissue ablation device. The system further including an ablation device identification component, wherein the ablation device identification component is configured to receive the captured image, generate a plurality of region proposals from the captured image, extract a plurality of feature vectors from the plurality of region proposals, wherein each feature vector of the plurality of feature vectors corresponds to a region proposal of the plurality of region proposals, determine a class for each region proposal of the plurality of region proposals, wherein determining the class for each region proposal is a function of the corresponding feature vector for the region proposal, and determine the position and orientation of the tissue ablation device as a function of the classes for each region proposal.

In another aspect, a method for ablation treatment of tissues, the method including receiving at least one tissue ablation device, wherein the tissue ablation device is communicatively connected to an ablation device controller and configured to control the ablation effect of the at least one ablation device. The method further including receiving, by an ablation device identification component from an imaging component, a captured image, wherein the imaging component is configured to capture the captured image and the captured image comprises a representation of the tissue ablation device. The method further including generating, by the ablation device identification component, a plurality of region proposals from the captured image. The method further including extracting, by the ablation device identification component, a plurality of feature vectors from the plurality of region proposals, wherein each feature vector of the plurality of feature vectors corresponds to a region proposal of the plurality of region proposals. The method further including determining, by the ablation device identification component, a class for each region proposal of the plurality of region proposals, wherein determining the class for each region proposal is a function of the corresponding feature vector for the region proposal. The method further including determining the position and orientation of the tissue ablation device as a function of the classes for each region proposal.

DETAILED DESCRIPTION

Exemplary embodiments of the present disclosure are described hereinbelow with reference to the accompanying drawings; however, it is to be understood that the disclosed embodiments are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

The exemplary embodiments of the present disclosure are described with respect to ablative therapy of a human, and some figures show images acquired on animals. It should be understood that the exemplary embodiments can be applied to the body, or portions of the body, whether human or animal.

Figure 1:
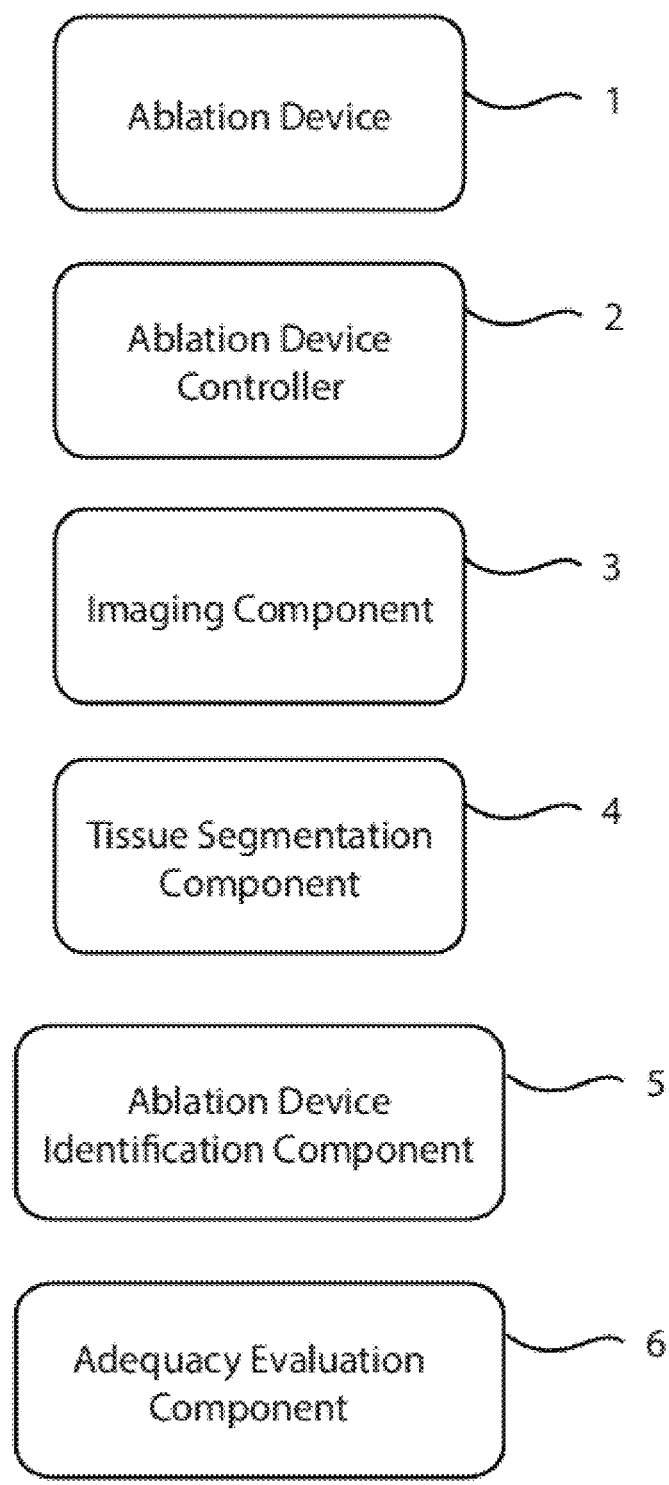
FIG. 1 depicts the system components of an exemplary embodiment of claim 1.

FIG. 1 depicts components of the ablation system object of the present invention.

Figure 2:
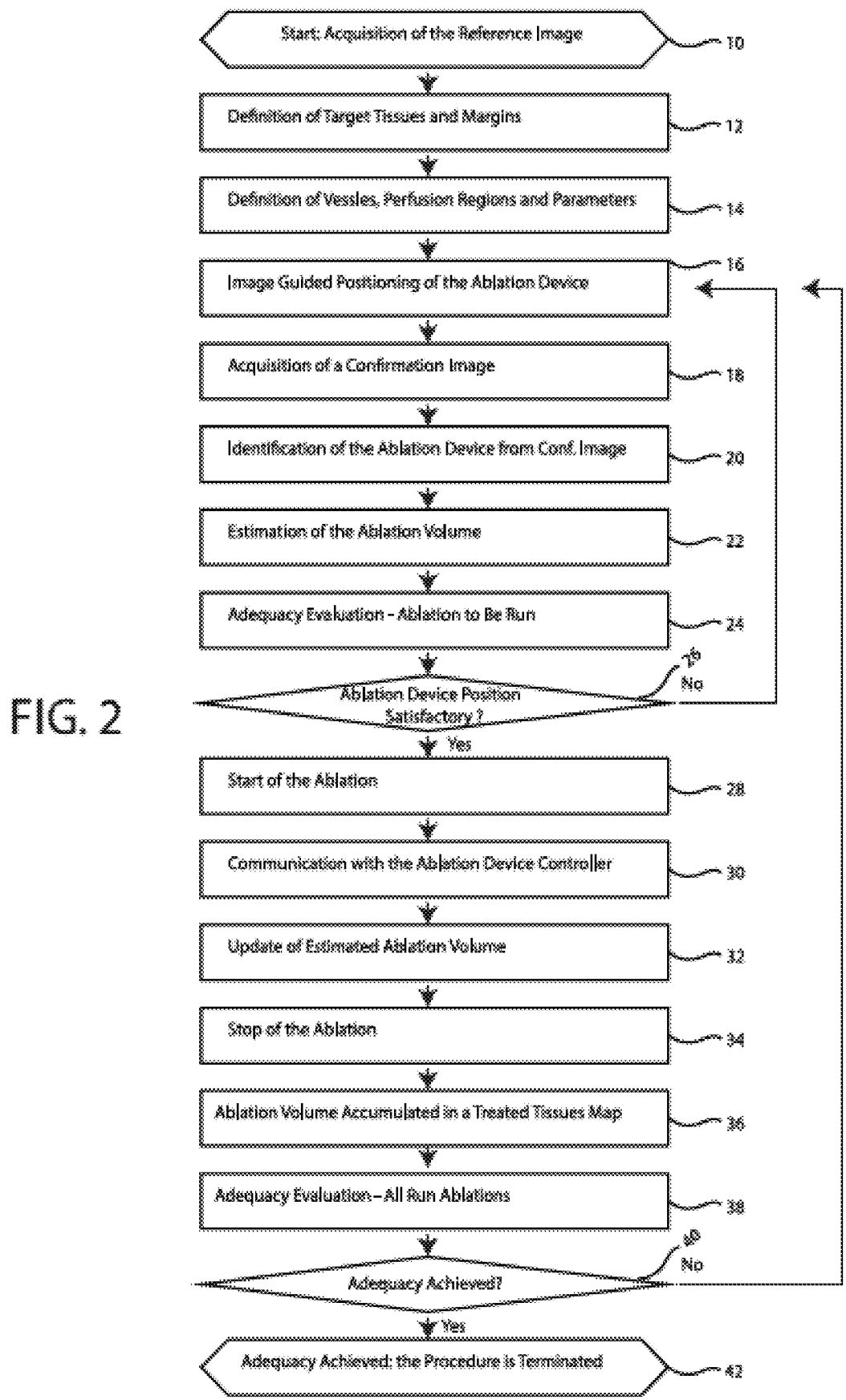
FIG. 2 depicts the flowchart for the operation of the exemplary system of claim 1.

FIG. 2 shows a flowchart representing the operation of the ablation system object of the present invention.

FIG. 1 depicts an overview of the ablation system according to various embodiments of the present disclosure. As shown in FIG. 1 the system includes an ablation device (1); this device can comprise a single or multiple RFA electrodes acting in monopolar or multipolar fashion, a single or multiple MWA antennas, a single or multiple IRE electrodes, a single or multiple cryo-probes, or a single or multiple devices able to ablate tissues thermally or by other means. The system comprises also an ablation device controller (2) which controls the ablation effect of to the ablation device (1) (e.g. by providing RF or microwave energy, by providing electric pulses for IRE, or by providing refrigeration for cryoablation probes). The ablation device controller (2) might optionally collect information that characterizes the tissues, such as the electrical impedance of tissues in RFA, indicative of the level of desiccation of tissues, the electro-magnetic reflection coefficient in microwave ablation, indicative of the level of desiccation of tissues, or other information about tissues which might me collected by the ablation probe controlled (2) from sensors mounted on the ablation device (1), like, for example, but not limited to, the temperature of tissues. As shown in FIG. 1 the system includes an imaging component (3) which allows capturing images of the patient, wherein such images can capture also the ablation device (1) as deployed in the tissues. The imaging component (3) can consist, for example, in a CT scanner, a US scanner, an MRI scanner, a FL system, or in other kinds of imaging systems. As shown in FIG. 1 the ablation system includes a tissue segmentation component (4). This component receives images from the imaging component (3) and allows a human operator, through a GUI, to define one three-dimensional image as a reference image. The reference image will be used by the tissue segmentation component (4) to segment different tissues, as described in the following, and subsequent images acquired by the ablation system, through the imaging component (3), will be spatially registered to this reference images, so that features identified in those subsequent images can be spatially referred to the tissues segmented in the reference image. The tissue segmentation component (4) allows the operator to manually, or with semi-automatic, or with automatic algorithms, to segment and define three-dimensionally the ablation target tissues. The tissue segmentation component (4) might additionally offer a functionality to automatically create tissue margins, of an operator specified thickness, around the previously defined target tissues. These tissue margins, if defined, are also a target tissue for the ablation. It is common, for example, in the treatment of cancer, to treat a certain thickness of margins around the tissues that are identified as malignant and that are to be treated.

Figure 19:
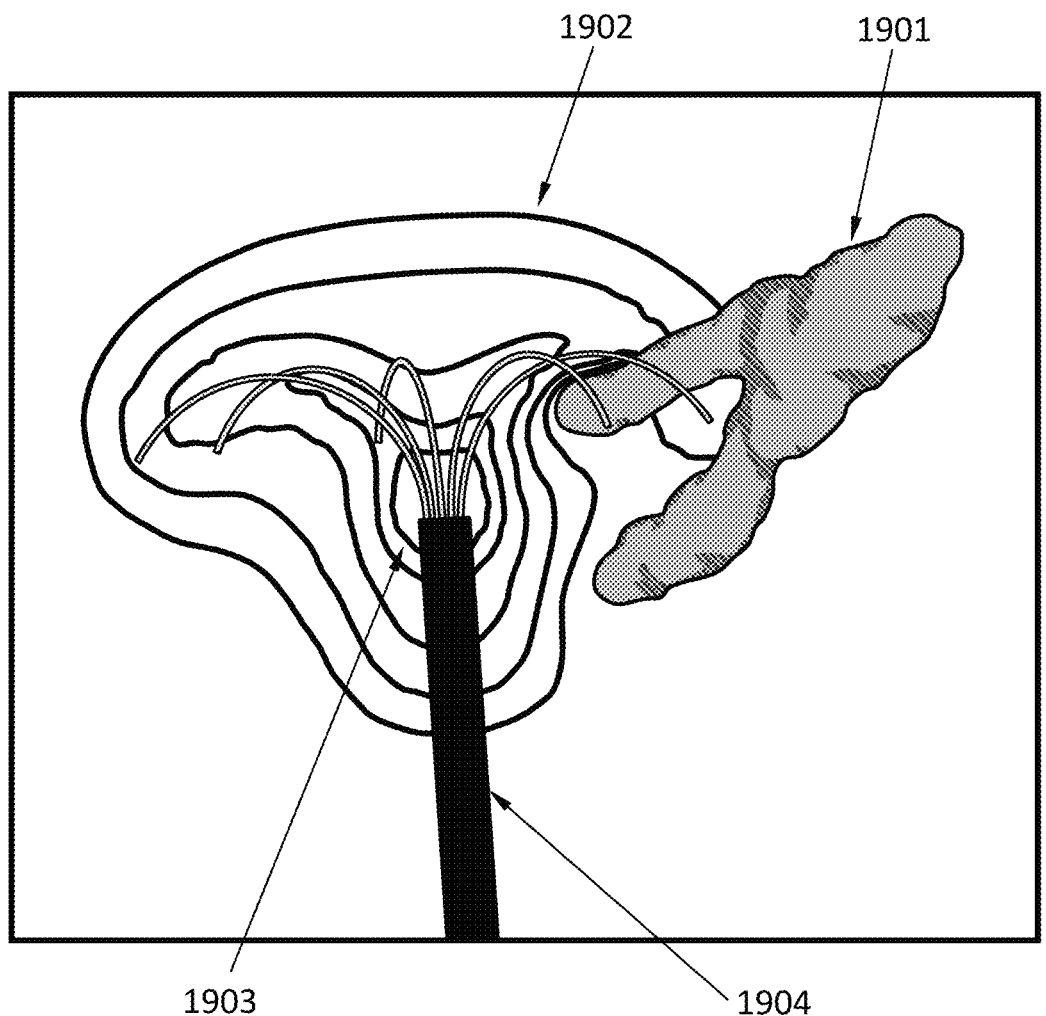
FIG. 19 depicts a CT slice to which have been superimposed an RFA electrode model and temperature isolines demonstrating the heat sink effect of a vessel on the temperature field.

Additionally the tissue segmentation component (4) might offer the functionality to segment three-dimensionally local vasculature. The segmented vasculature will optionally be used by the adequacy evaluation component (6) to account for the heat-sink effect of vessels and more accurately estimate the ablation volume, as discussed later and as illustrated by FIG. 19. Additionally the tissue segmentation component (4) might offer the functionality to segment three-dimensionally different regions of tissues and to specify the perfusion rates for the defined tissue regions. This information will optionally be used by the adequacy evaluation component (6) to more accurately estimate the ablation volume. Perfusion is a phenomenon that removes heat from the ablation site, and higher or lower rates of perfusion result in smaller or larger ablation volumes respectively. Additionally the tissue segmentation component (4) might use images to estimate perfusion rates and regions of tissues with different perfusion rates, as an alternative to user input, or in addition to user input.

The ablation device identification component (5) is a component that uses automatic image processing algorithms, or semi-automatic image processing algorithms, or manual processes, where the operator might provide input through a GUI, to identify the intracorporeal position and orientation of the ablation device (1) and optionally to identify, for ablation devices that might be subject to deformations, the geometry of the ablation device (1) as deployed in the tissues. The intracorporeal position and orientation of the ablation device (1), and optionally the identified geometry of the ablation device (1), are fed to the adequacy evaluation component (6) and will be used to build a map of treated tissues as discussed later.

Identifying the position and orientation of the ablation device (1) solely from images is an advantageous embodiment, as other ablation systems are based on surgical tool tracking technologies, where the ablation device position and orientation is tracked by optical, electromagnetic, or ultrasound means using dedicated hardware and software components. The addition of these tracking components to the ablation system is expensive, increases clutter in the operating room, might pose restrictions on the movement of the operator, and requires generally the use of dedicated ablation devices that integrate with the specific tracking technology.

Figure 4:
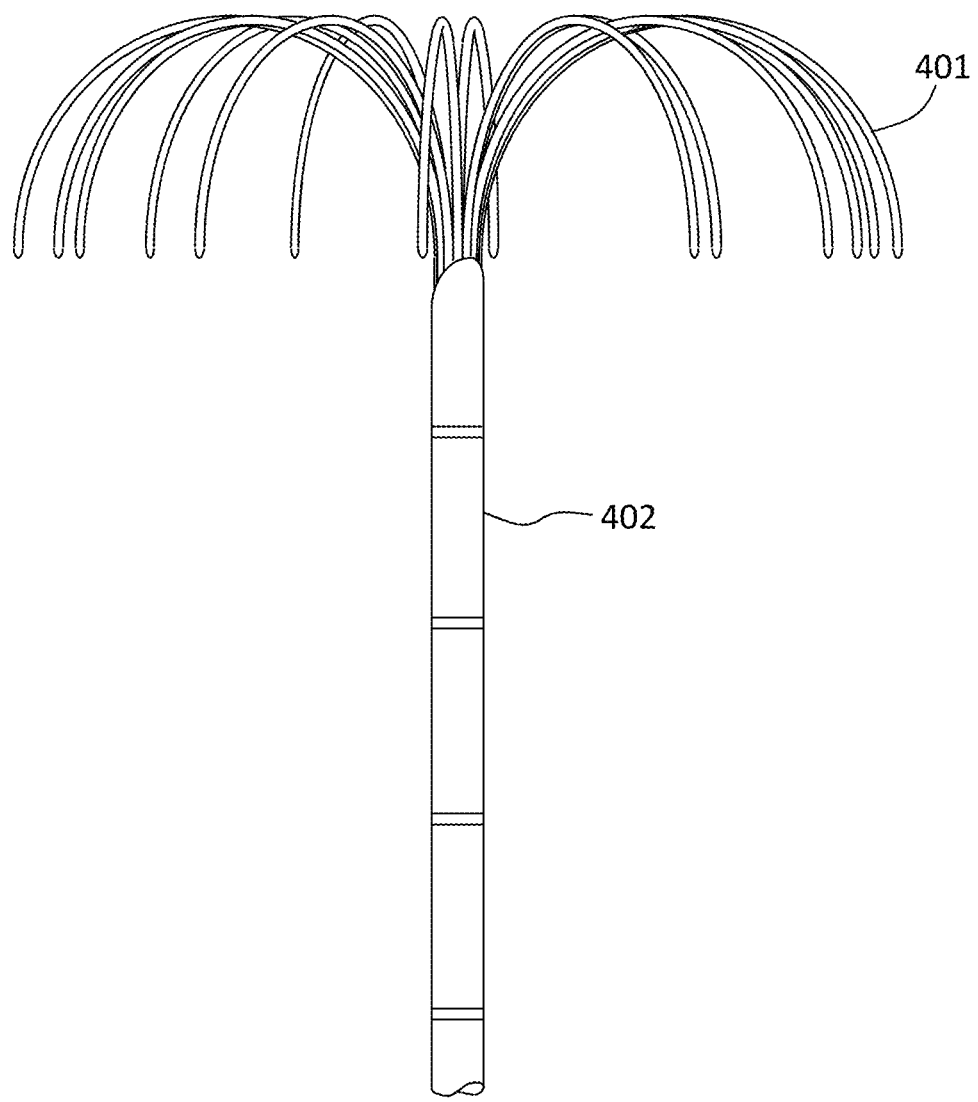
FIG. 4 depicts an example of a common commercial RFA electrode which deploys tines.

Certain ablation devices comprise flexible parts, or otherwise parts that are rigid, but which are mechanically connected by flexible joints. As an example, FIG. 4 shows, as an example, a commercial RFA electrode formed by a hollow shaft (402) which is inserted into the tissues, and by 14 tines, which deploy in an umbrella fashion—(401) indicates one tine. Tines are metallic filaments that are housed inside the shaft during device insertion. Tines are deployed in the tissues after insertion in order to create a larger volume of ablation. Tines are formed by shape-memory metal, and once deployed, each of them should in principle form the arch of a semi-circle. Tines should also, in principle, deploy with regular angles around the shaft between any two tines. For example, for an electrode with 14 tines the angle around the shaft between any two tines should be 360/14=25.7 degrees. As tines are thin metallic filaments, they are subject to deformation when deployed in tissues, and, besides other forms of deformation, the angle around the shaft between any two tines is usually not regular and can change significantly between different pairs of tines.

These changes in the geometry of the ablation device (1) when deployed in tissues, which are normally not considered, affect the ablation volume of the ablation device (1).

In this advantageous embodiment the ablation device identification component (5) implements functions for identifying the intracorporeal position and orientation of the ablation device (1), and, for ablation devices which might be subject to deformation, functions for identifying the geometry of the ablation device (1) as deployed in the tissues. This identified ablation device (1) geometry will be used by the adequacy evaluation component 6) to update the estimated ablation volume of the ablation device (1), based on the deployed geometry of the ablation device (1).

Figure 3:
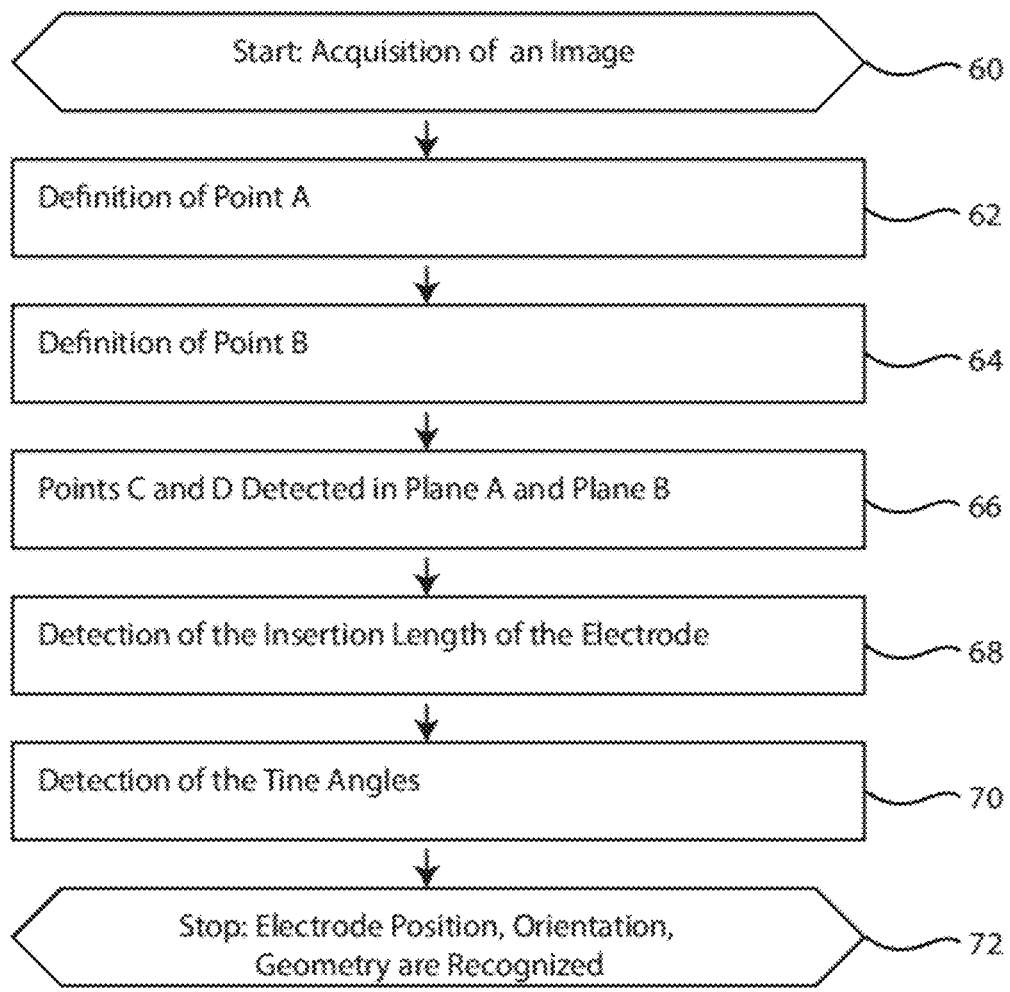
FIG. 3 depicts the flowchart of an exemplary embodiment of an algorithm able to able to recognize in CT images the position and orientation of an RFA electrode, and the angle around the shaft of the electrode to which each tine deploys.

FIG. 3 illustrates a flowchart of an exemplar embodiment of an algorithm for semi-automatically locating RFA electrodes similar in shape to electrode in FIG. 4 and for identifying the angle of deployment around the shaft of each tine of the electrode from analysis of CT images. This embodiment is merely an example of the disclosure and may be embodied in various forms, using different image analysis algorithms and with algorithm designs that are specific to different ablation devices from the ablation device considered in this embodiment; finally this embodiment is demonstrated on CT images acquired on animals, application to humans is identical, and we do not intent to limit by any means the scope of this embodiment, even if disclosed simply for exemplar purposes, to animals.

Many common ablation devices on the market may be rigid. When the shaft of an ablation device is rigid, in order to describe the shaft, it is sufficient to detect the end points (for example, a proximal end and a distal end). However, when a shaft is flexible, one or more intermediary points may be needed to be detected in order to adequately describe the position of the shaft. This is due to the possible curvature in the flexible shaft. Some ablation devices may also deploy tines, similarly, intermediary points along the tines may need to be detected in order to locate the tines. In some embodiments, for example where the tines are shaped as an arc, fewer intermediary points may be needed, because the shape of the arc may be used for interpolation.

Figure 5:
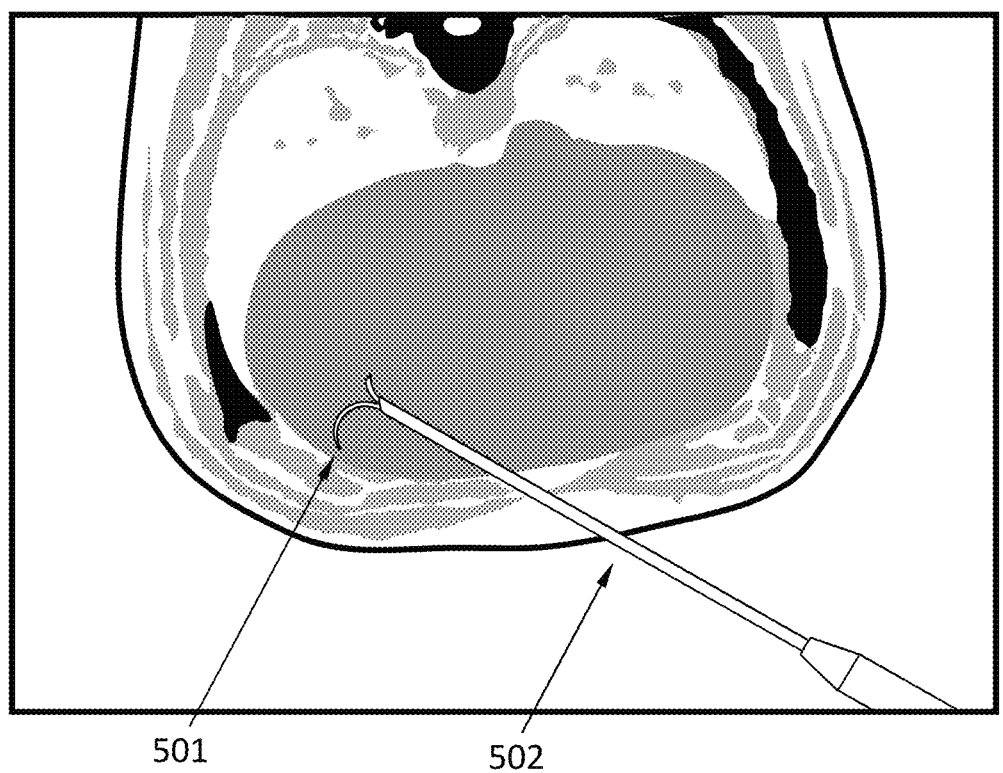
FIG. 5 depicts a CT scan of an RFA electrode deployed in tissues.

FIG. 5 shows a CT image of an RFA electrode with tines deployed in the tissues of an animal. The image is a 2D slice of a 3D CT volume. The slice passes by the shaft of the RFA electrode (501) and intercepts one of the tines (501), which is visible as a semi-arch.

Figure 6:
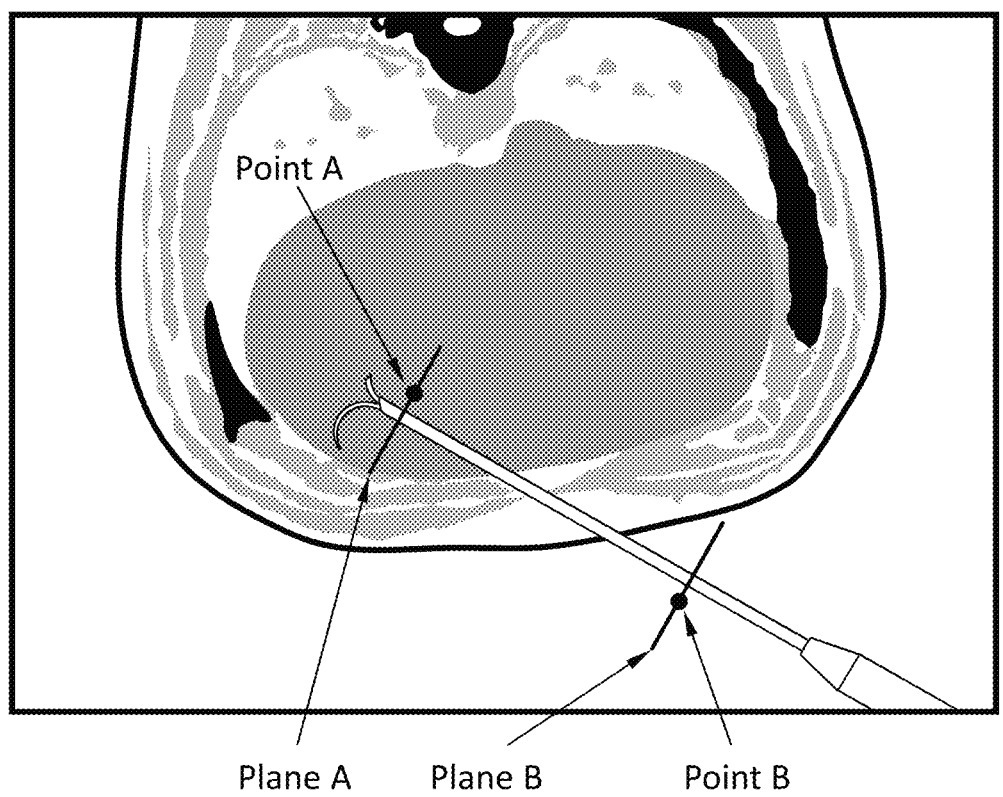
FIG. 6 depicts the CT scan of FIG. 5 where two input points provided by an operator are shown.

Switching to the flowchart of FIG. 3, the electrode identification algorithm starts with the acquisition with the imaging component (3) of an image capturing the RFA electrode deployed in the tissues (step 60). The operator, using a GUI, is shown 2D views of the image and using a GUI and an input device, like, for example a computer mouse or a trackpad, clicks on a point near the distal end of the ablation device (step 62); we label this point as "Point A". FIG. 6 depicts a Point A, which has been rendered as a black circle for illustration purposes. Point A has been depicted proposely off the center of the shaft of the electrode, as the user is required only to click in the proximity of the distal end of the electrode, but not exactly on the electrode. As the position of the 2D slice relative to the 3D image volume is known, this operation defines the 3D coordinates of Point A. Through the same GUI, input device, and method, the operator will click on a 2D slice, which can be different from the previous slice defining point A, near the proximal end of the ablation device (1) defining a "Point B" (step 64) as illustrated in FIG. 6. This operation defines the 3D coordinates of Point B. In some embodiments, the shaft may also have an intermediary point. In some embodiments, the shaft may be a shaft of an electrode as described above. The intermediary point may be located between the proximal end and the distal end of the shaft. In some embodiments, the intermediary point may be located halfway between the proximal end and the distal end of the shaft. In some embodiments, the intermediary point may be ⅓ of the way from the proximal of the shaft. In some embodiments, the intermediary point may be ⅔ of the way from the proximal of the shaft. In some embodiments, the shaft may include a plurality of intermediary points. In some embodiments, the plurality of intermediary points may be equally spaced between the proximal and distal end of the shaft. In some embodiments, the plurality of intermediary points may be closer together at areas of higher curvature. In some embodiments, the shaft may flex. Accordingly, the location of the intermediary points may be identified in order to determine the describe the shaft.

Point A and Point B define a line passing by the two points, Line AB, which is an approximation to the axis of the shaft of the electrode, as the operator is required to pick the two points only in the proximity of the shaft, but not on the shaft. The next steps of the electrode identification algorithm aim to identify the exact axis of the RFA electrode shaft.

The electrode identification algorithm computes the Line AB from Point A and Point B. The electrode identification algorithm defines a plane passing by point A, and normal to Line AB, labeled plane A, and a plane passing by point B and normal to Line AB, labelled Plane B. These planes are used for sampling the image intensity. By construction the two planes are likely to intersect the shaft of the electrode in the CT 3D image, as visible in FIG. 6, where the planes are indicated by two white segments. The planes are constructed to have a finite extension, bounding them to, for example, 3 cm respectively from Point A and Point B. Bounding the planes makes them likely to intersect the shaft of the electrode, if the operator picked Point A and Point B not exceedingly far from the shaft of the electrode, and at the same time unlikely to intersect other structures, in the image, that have a high CT intensity as the metallic electrode shaft.

Figure 7:
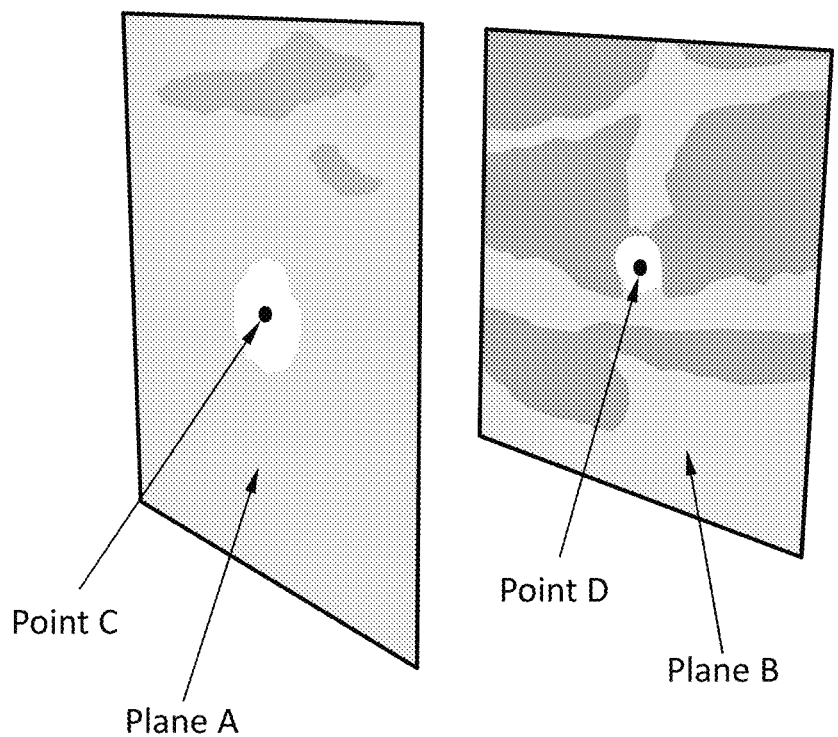
FIG. 7 depicts two sampling planes that are used to sample the intensity values of a CT volume image capturing a deployed RFA electrode.

The CT image values, sampled on Plane A and Plane B, is illustrated in FIG. 7. A high intensity spot results at the location in the planes where the shaft of the electrode is intersected, being the shaft metallic. Locating of the maximum intensity point on plane A defines a Point C in space, which is on or near the center of the electrode shaft, and near the distal end of the electrode. Locating of the maximum intensity point on plane B defines a Point D in space, which is on or near the center of the electrode shaft, and near the proximal end of the electrode, this is step 68 of FIG. 3.

Figure 8:
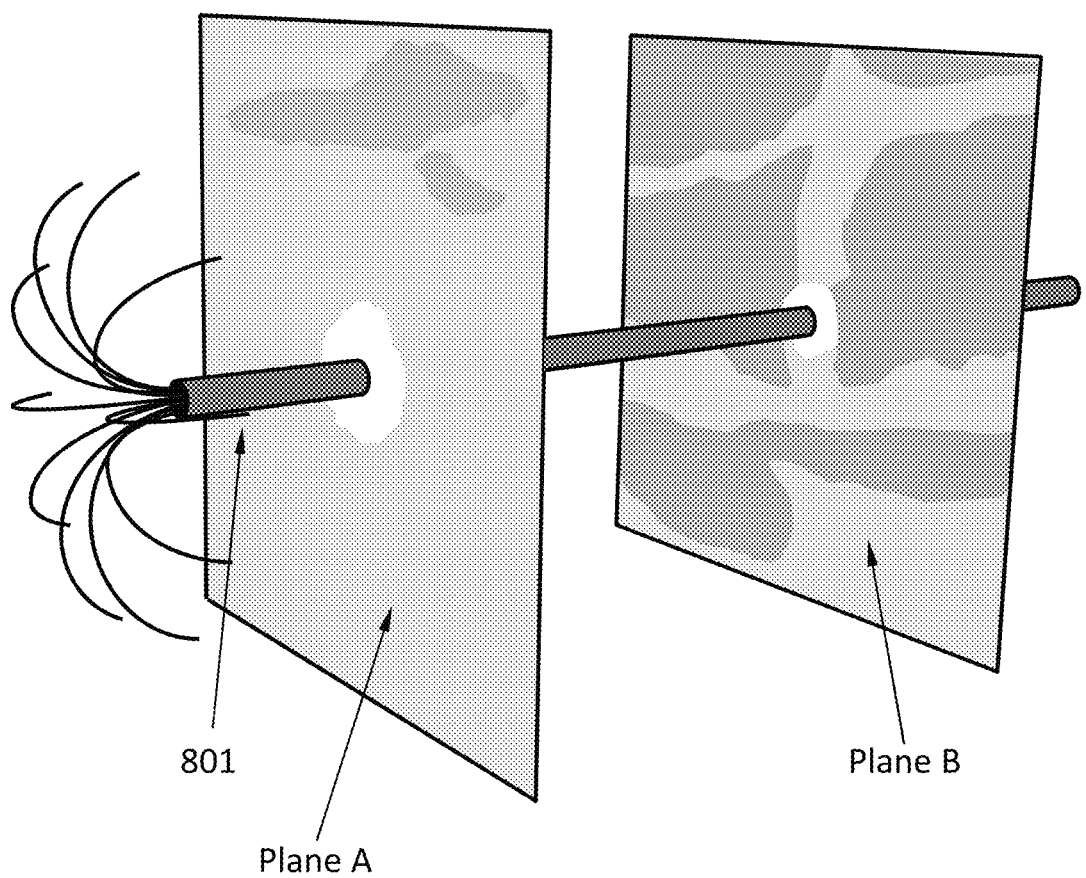
FIG. 8 depicts the two sampling planes of FIG. 7 with the addition of an RFA electrode model to better illustrate the spatial relationship.

The line "Line CD", passing by the points Point C and Point D, is therefore a good estimation of the axis of the electrode shaft, as points Point C and Point D are on the shaft of the electrode. In FIG. 8 a computer model of an RFA electrode (801) has been rendered together with Plane A and Plane B to illustrate spatial relationships. The computer model of the electrode has been built with its shaft passing by Point C and Point D, as the real electrode captured by the CT image.

The preceding algorithm steps have estimated a line, Line CD, representing the axis of the electrode shaft as in the tissues. Additionally to these steps, full determination of the position of the electrode requires determining the position of the electrode along Line CD, or how deep the electrode has been inserted in the body along Line CD. This can be achieved locating, for example, in the image the point along Line CD where the tines attach to the electrode shaft. For this purpose, the electrode identification algorithm defines a cylindrical surface over which the intensity of the image is sampled, this allows estimating such point, as discussed next.

Figure 9:
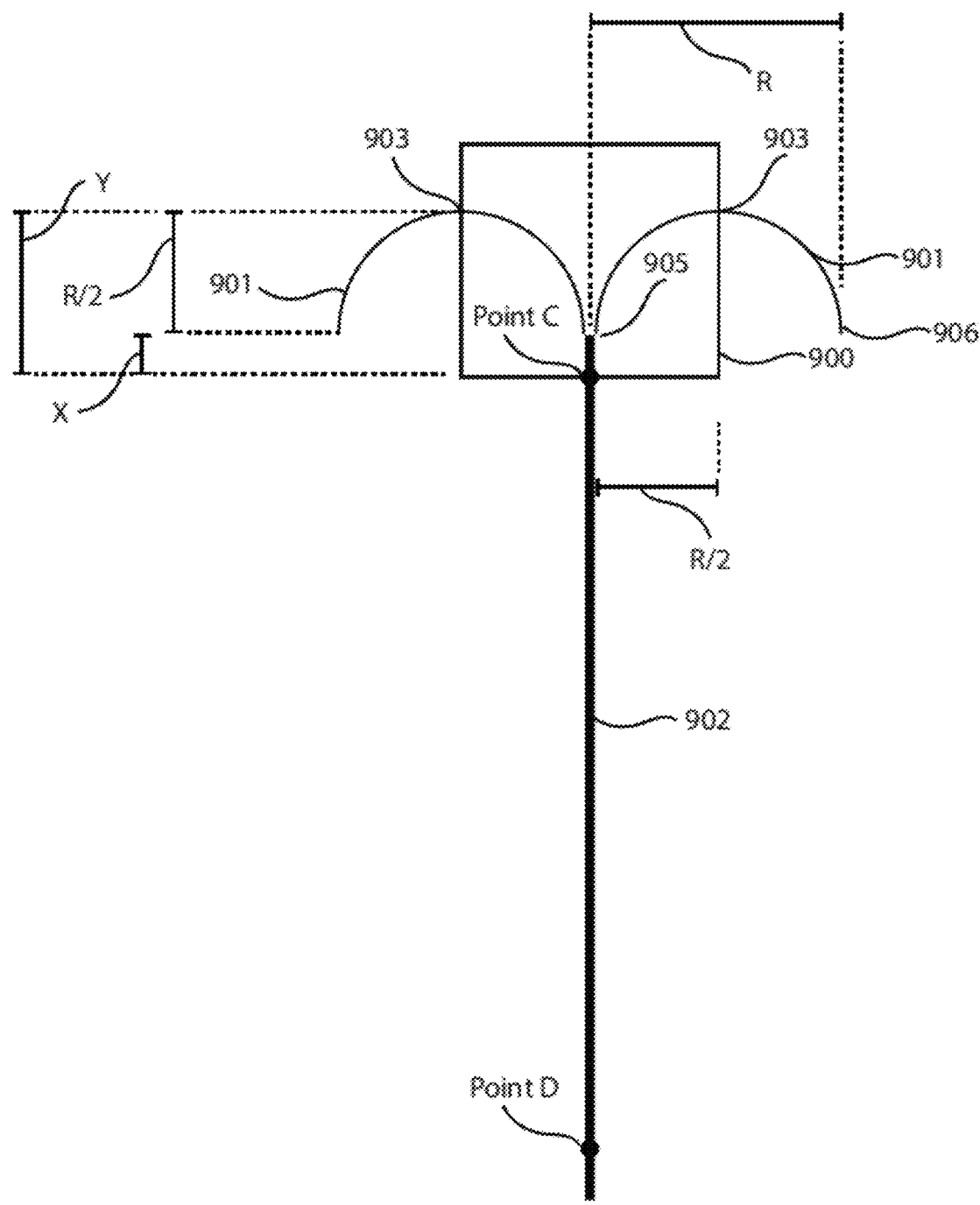
FIG. 9 depicts the geometry of a sampling cylindrical surface used to sample the intensity values of a CT volume image capturing a deployed RFA electrode.

FIG. 9 shows the shaft of the electrode (902), Point C and Point D as identified by the preceding steps and laying on the shaft, two tines (901) of the multiple tines the electrode might have. In some embodiments, the tines of an RFA electrode (902) may be radially attached to the shaft of electrode (902). In some embodiments, the tines of electrode (902) may be spaced apart radially at an equal angle from each other. As a non-limiting example where there are four tines (901), the tines (901) may be located at 90-degree angles from each other. As a non-limiting example where there are six tines (901), the tines (901) may be located at 60-degree angles from each other.

The objective of this next step is to determine the offset X, along Line CD, between the point C and the point where the tines attach to the electrode (905). This offset determines the position of the electrode along Line CD, and therefore completely the position and orientation of the electrode, together with Line CD which is known at this point.

As a non-limiting example, tines (901) of an electrode may be semi-circles with a distance between the tip of the tine (906) and the point where they connect to the shaft of the electrode (105) of R. In some embodiments, this electrode may be an RFA electrode. In some embodiments, the point (905) where the tines (901) connect to the shaft of the electrode (105) may be referred to as an attachment point (905). Furthermore, in some embodiments, the tip (906) of tine (901) may be referred to as the free end (906) of tine (901). In some embodiments, the free end (906) may be at an opposite end of tine (901) from the attachment point (905). In some embodiments, a tine (901) may have a tine intermediary point, wherein the tine intermediary point is located on a tine (901) between the attachment point (905) and the free end (906). In some embodiments, tine intermediary point may be located halfway between attachment point (905) and free end (906) on the body of tine (901). In some embodiments, tine intermediary point may be located between attachment point (905) and free end (906) on the body of tine (901), such that it is ⅓ of the distance from attachment point (905) and free end (906). In some embodiments, tine intermediary point may be located between attachment point (905) and free end (906) on the body of tine (901), such that it is ⅔ of the distance from attachment point (905) and free end (906). In general, tine intermediary point may be located anywhere on tine (901) between attachment point (905) and free end (906). In some embodiments, there may be a plurality of tine intermediary points on tine (901) between attachment point (905) and free end (906). In some embodiments, the plurality of tine intermediary point may be equally spaced between attachment point (905) and free end (906). In some embodiments, the plurality of intermediary points may have a higher concentration at critical areas of tine (901). As a non-limiting example, there may be a greater concentration of intermediary points closer to the free end (906) or tine (901). As another non-limiting example, there may be a greater concentration of intermediary points in areas of tine (901) with a higher curvature. The item (900) represents the cylindrical surface used for sampling the image. The cylinder (900) is coaxial with Line CD, has a base that passes by point C and extends vertically for a certain extension, for example R. The requirement is that the height of the sampling cylinder is greater than Y, or X+R/2, so that the cylinder is guaranteed to intersect the tines of the electrode at points 903. Point C is in the proximity of point 105 (the operator is requested to define a Point A in the proximity of the distal end of the electrode, and point C results in the neighborhood of point A)—so a height of the cylinder of R is likely to be sufficient for the tines to intersect the lateral surface of the cylinder at points 903, as in FIG. 9. The radius of the cylinder is defined to be R/2, so that the cylinder will intercept the tines at points 903 that are at the apex of the times; using a cylinder radius of R/2 determines therefore that the intersection points 903 have an offset from point 905 of R/2 along the Line CD, and that Y=X+R/2.

Figure 10:
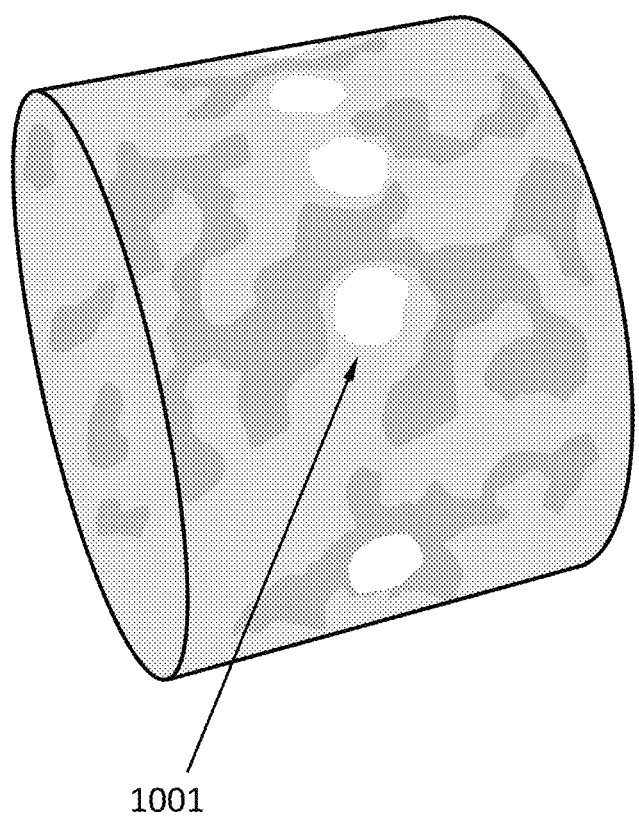
FIG. 10 depicts a sampling cylindrical volume which has been used to sample the intensity values of a CT volume image capturing a deployed RFA electrode.

FIG. 10 shows a sampling cylinder used to sample the CT image in FIG. 6 according to the above procedure. The image intensity values on the surface of the cylinder present local high intensity spots at the points where each tine intersects the lateral surface of the cylinder, as the tines are metallic. One of these intersection spots is labeled (1001) for illustrative purposes. The spots are not evenly spaced around the cylinder, reflecting the uneven deployment of the tines.

Detection of the local maxima of the intensity values over the surface of the cylinder allows determining the longitudinal position of the tines along Line CD, as well as the angular position around the line CD.

The image intensity values sampled on the sampling cylinder (900) can be expressed in cylindrical coordinates (z, 8) where z is a longitudinal coordinate along Line CD, with Point C as origin, and 8 is the angular position around Line CD. This allows representing the sampled values in the plane (z, 8) as in FIG. 11.

As in FIG. 10, intersections of the tines in the image with the sampling cylinder surface, now flattened in the (z, 8) plane, result in bright spots as (1101). Summing the values in the sampled image of FIG. 11 over pixel columns of the image, results in a vector of values which is plotted in FIG. 12, where the intensities (unit of measure Hounsfield Unit, HU) of the single local maxima in FIG. 11 add up, as they are vertically aligned, or close to aligned, giving rise to a single peak value in the vector of sums over pixel columns. The abscissa of the peak in FIG. 12 (1201) reflects the distance, along Line CD, between the point C and the intersection points (903) of FIG. 9, or Y of FIG. 9. This allows determining X as Y−R/2, where R is the radius of the electrode's umbrella of tines, as in FIG. 9. Therefore the position of point 105, where the tines attach to the electrode is completely known. This, together with knowledge of LineCD, determines completely the position and orientation of the electrode in the image.

Figure 13:
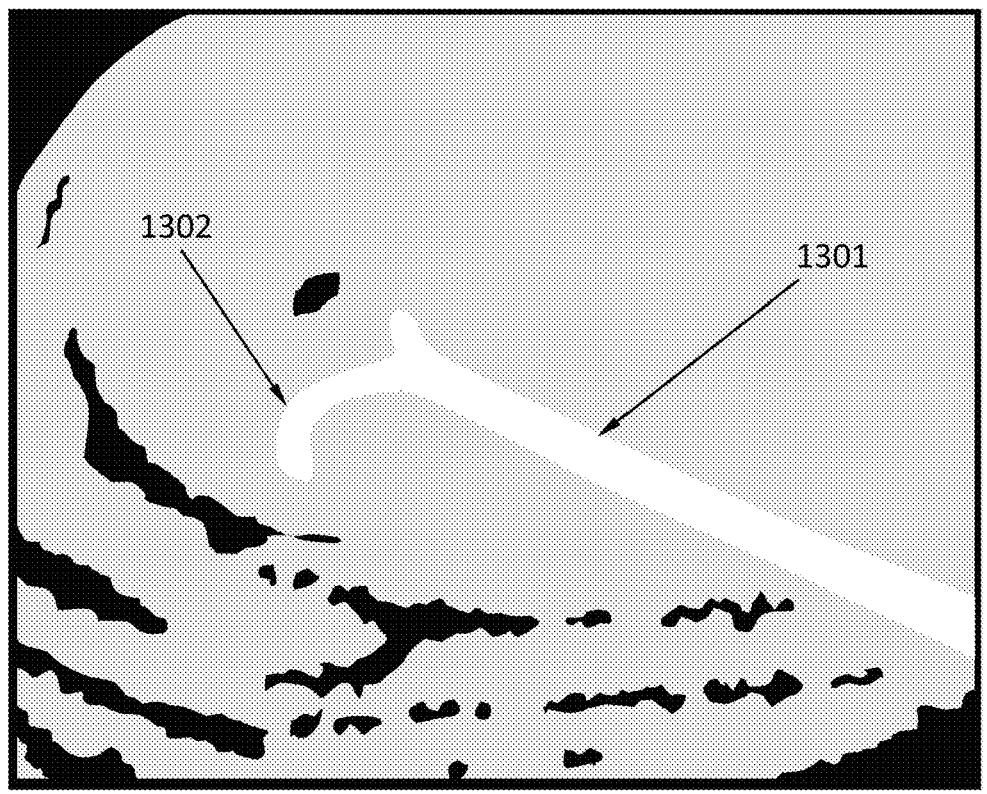
FIG. 13 depicts the detail of a CT image of an RFA electrode deployed in tissues.
Figure 14:
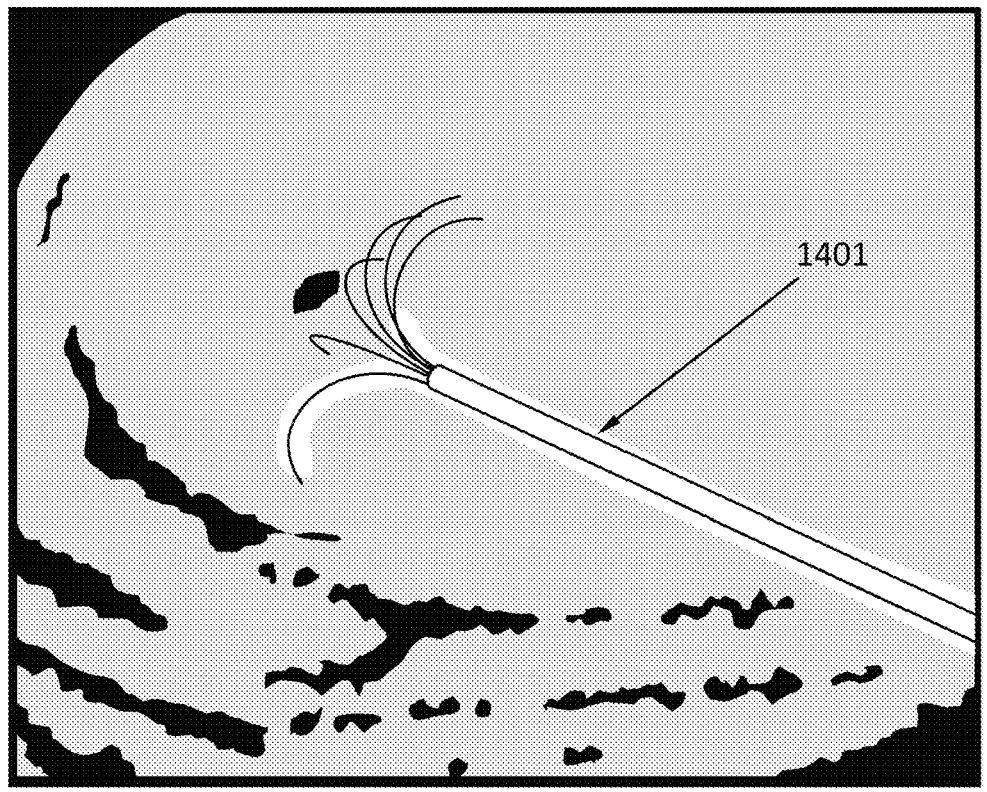
FIG. 14 depicts the CT image of FIG. 13, where of model of an RFA electrode has been rendered at a spatial position and orientation matching those of the true electrode visible in FIG. 13.

FIGS. 13 and 14 demonstrate this above step of the electrode position and orientation identification algorithm, which is labeled as step 68 in the flowchart of FIG. 3. FIG. 13 shows a view of a 2D slice of a 3D CT image of a deployed RFA electrode, where the image slice intercepts the electrode shaft (1301) and one of the tines (1302). The preceding steps of electrode identification algorithm have been applied to the full 3D image to locate the electrode. The resulting known position and orientation of the RFA electrode allow to render in FIG. 14 a computer model of the electrode (1401) correctly positioned in the image, at a location and orientation which coincide with the physical electrode position and orientation.

The next step of the electrode identification algorithm in the flowchart of FIG. 3 is step 70, which aims at detecting the angular position of each tine around the shaft of the electrode, or equivalently around line CD.

Figure 11:
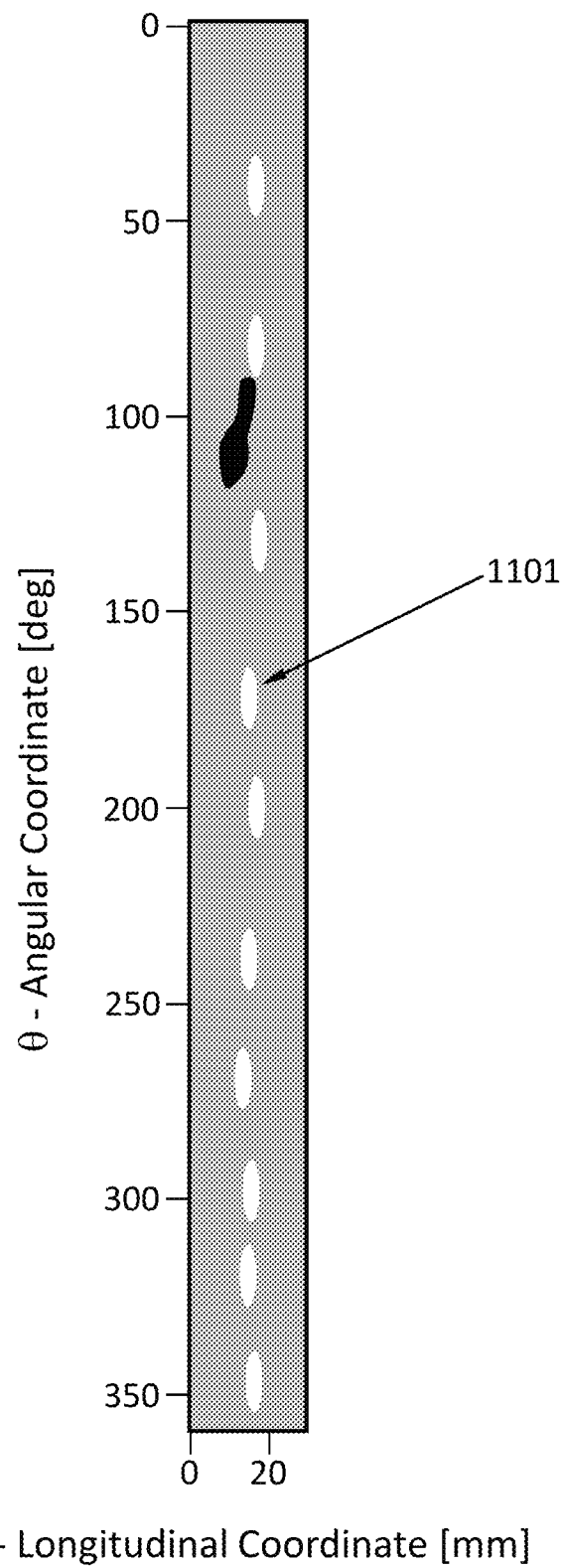
FIG. 11 depicts the CT intensity values sampled on the sampling cylinder of FIG. 10 but represented "flattened" in a plane.
Figure 12:
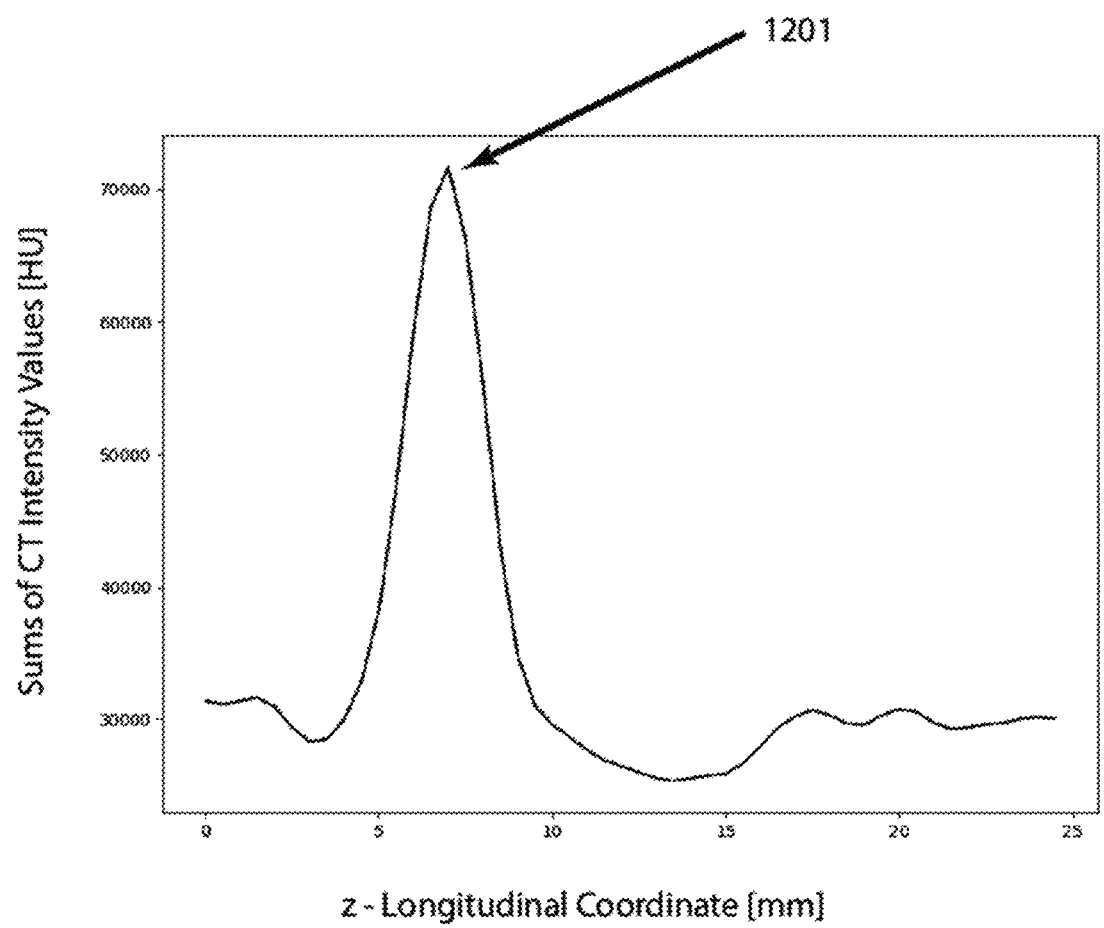
FIG. 12 depicts data values obtained by summing by columns the pixel intensities from FIG. 11.
Figure 15:
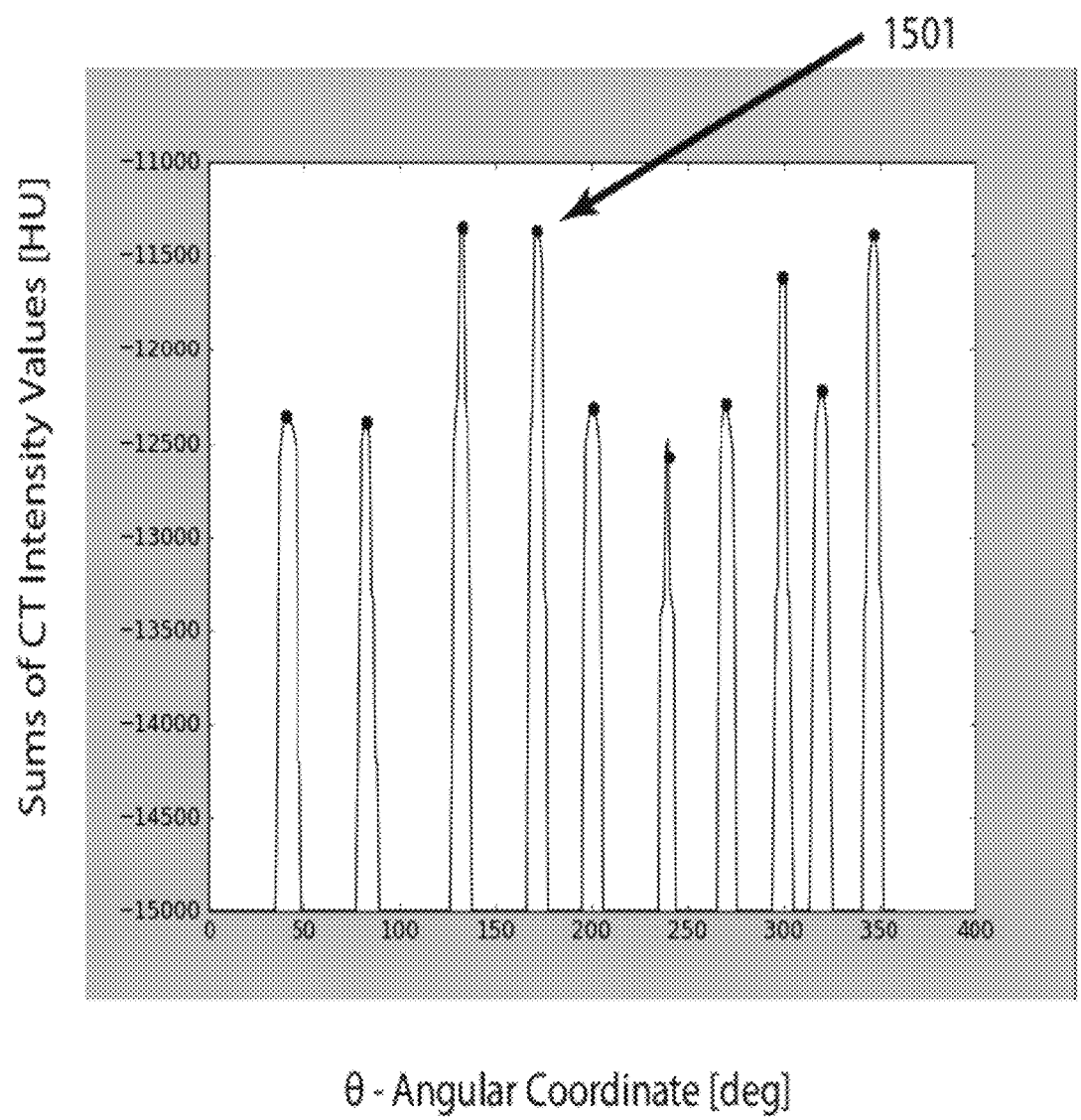
FIG. 15 depicts data values obtained by summing by rows the pixel intensities from FIG. 11.

The ordinate of the local maxima of the CT intensity sampled on the sampling cylinder, as in FIG. 11 represents the angle of each tine around the shaft of the electrode. FIG. 15 shows a plot of a vector of values obtained by summing by pixels rows the intensity values in the image of FIG. 11. The vector may include a threshold, setting to zero any values that fell below 50% of the maximum value found in the vector. The abscissa of the local maxima in this vector corresponds to the ordinate of the local maxima in FIG. 11. The electrode identification algorithm identifies the local maxima in this vector and determines in this way the angular coordinate of each single tine of the electrode.

Figure 16:
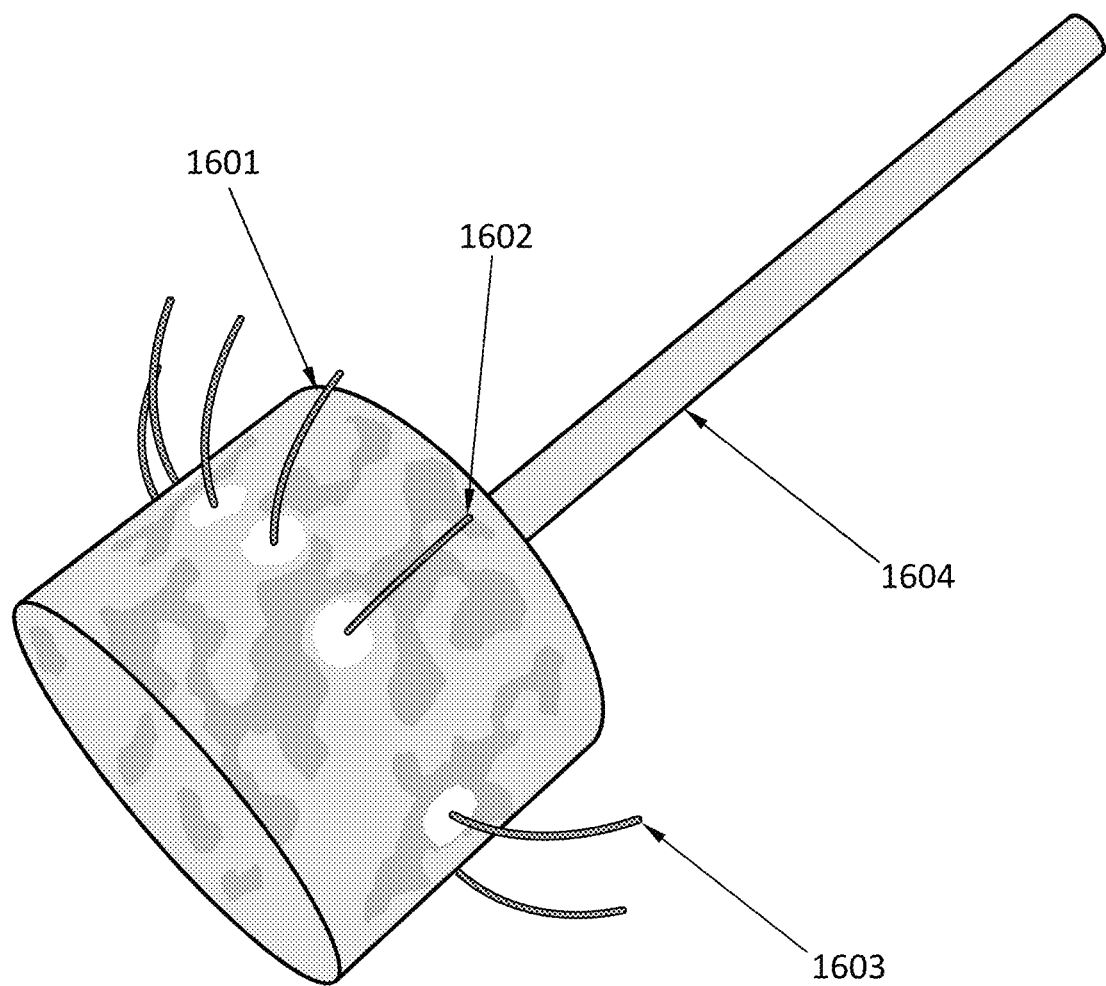
FIG. 16 depicts the sampling cylinder of FIG. 10 with the addition of an RFA electrode model to better illustrate the spatial relationship.

FIG. 16 illustrates the sampling cylinder of FIG. 10 where a computer model of and RFA electrode has been added to the rendering (1604). This electrode model has been built with tines matching the detected tine angles. As it is possible to appreciate, the tines of the model pass by the high intensity spots on the sampling cylinder, matching therefore the angular position of the tines of the true electrode as deployed in the tissues. This figure also illustrates the fact that the angles between tines may be unevenly distributed. For instance, the angle between tine (1603) and tine (1602) is greater than the angle between tine (1602) and tine (1601).

Figure 17:
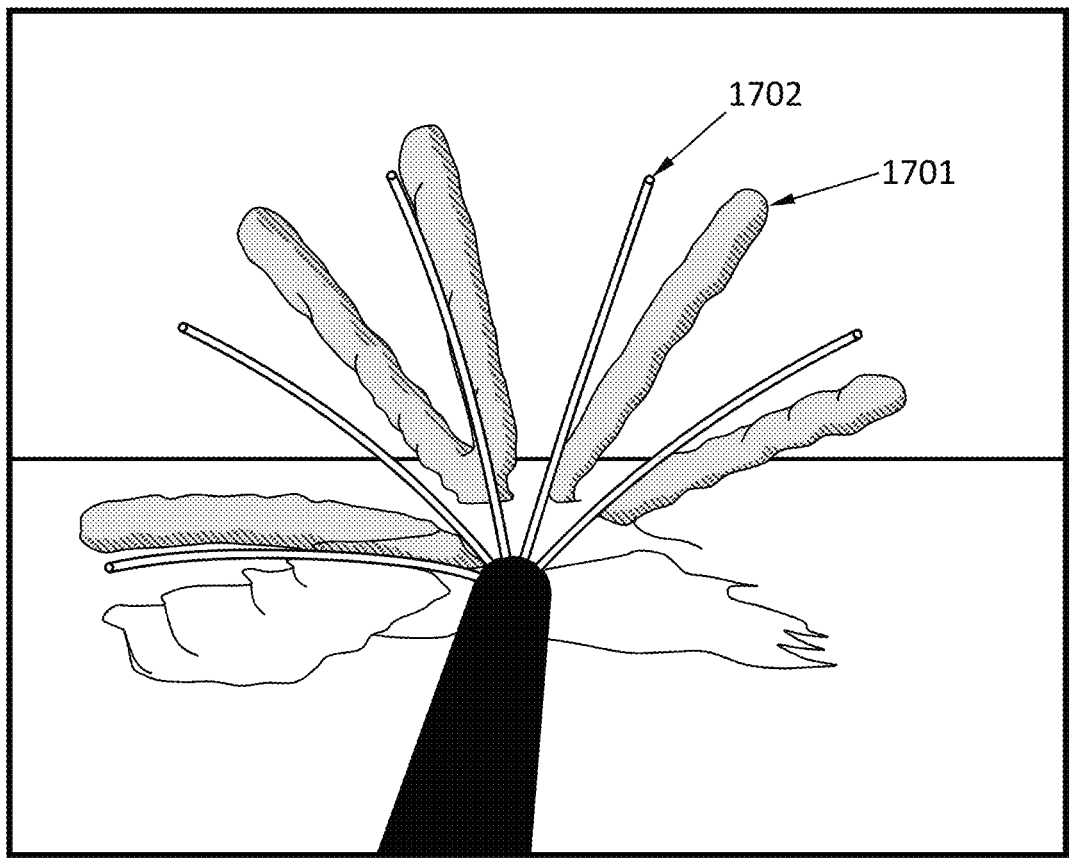
FIG. 17 depicts a CT data threshold to highlight the tines of an RFA electrode, and a computer model of an RFA electrode which has been built with a regular geometry of the tines.
Figure 18:
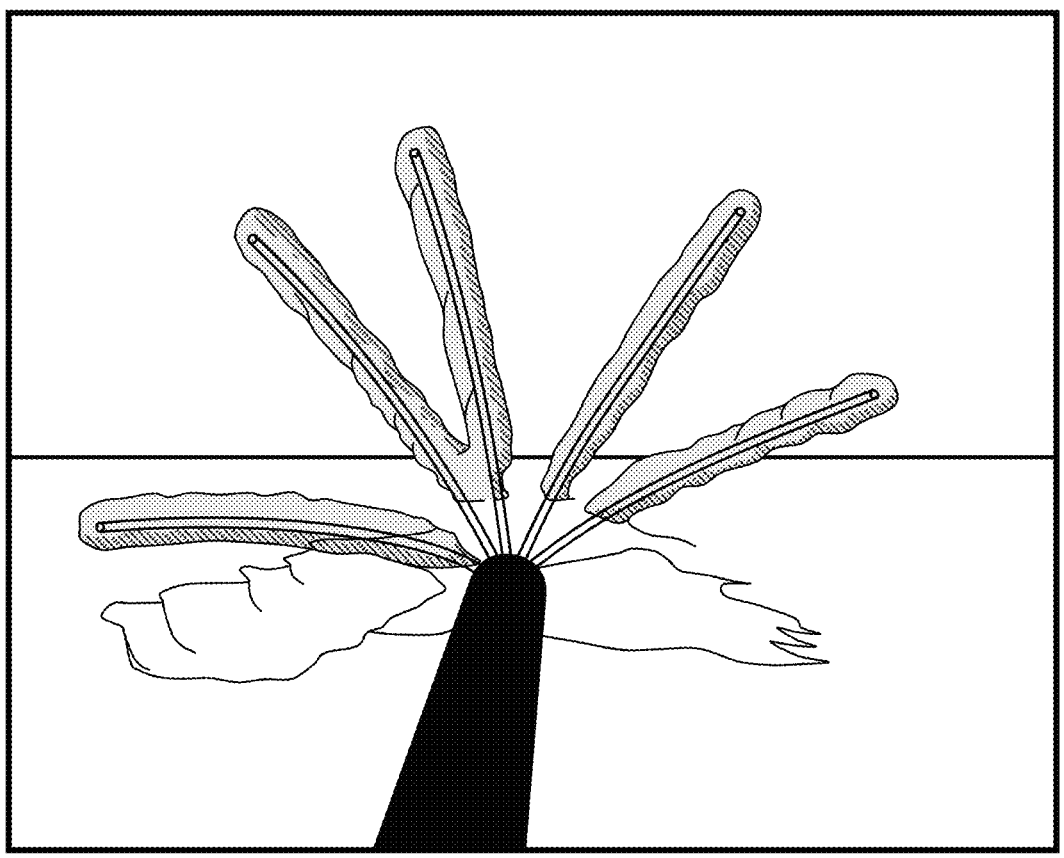
FIG. 18 depicts a CT data threshold to highlight the tines of an RFA electrode, and a computer model of an RFA electrode which has been built with a geometry of the tines matching the true geometry of the RFA electrode captured from the CT image.

FIGS. 17 and 18 further demonstrate the electrode identification algorithm. FIG. 17 shows a 2D slice of a CT 3D image intercepting the electrode shaft. The figure illustrates threshold values from the underlying 3D CT image (1701), where the threshold level was set to be high enough not to include tissues, but only the metallic probe tines, which have a high CT value. Superimposed to this image is the computer model of one RFA electrode, for which the position and orientation in the image have been determined with step 68 of the electrode identification algorithm, but where the angular distribution of the tines has been assumed to be regular. The specific electrode has 10 tines, and an angle between each two tines of 360/10=36 degrees was assumed. Clearly the model does not match the actual position of the tines in the tissues. The tines of the model (1702) do not align with tines in the CT image (1701).

FIG. 18 shows the same information, but the RFA electrode model has been updated to reflect the true angular position of the tines as identified by step 70 of the electrode identification algorithm. Clearly tines of the model match well the position of the true tines of the electrode as deployed in the tissues, and as captured by the CT image. The angles between any two tines are irregular. The updated electrode model can be used to estimate an ablation volume for the deployed electrode which is representative of the true geometry of the deployed electrode.

The electrode identification algorithm terminates at step 70, as the position and orientation of the electrode, and the angular position of each tine are recognized.

The above paragraphs have described an exemplar embodiment of an electrode identification algorithm part of the ablation device identification component (5). Previous paragraphs have also described the components that are part of the ablation system in FIG. 1 with the exception of the adequacy evaluation component (6).

The aim of adequacy evaluation component (6) is to highlight, with computer graphics, on a GUI, at any stage of a procedure, where one or multiple ablations are performed, which target tissues and margins have been treated and which not, in such a way that the adequacy can be evaluated in a visually and immediate manner.

The adequacy evaluation component (6) is best described following the flowchart of FIG. 2. In the next therefore the flowchart is illustrated, and the adequacy evaluation component (6) is described.

At step 10 the operation of the ablation system starts, and a suitable image of the patient is acquired. The image is fed to the tissue segmentation component (4) and defined as a reference image. The adequacy evaluation component (6) initializes a tissue damage map to have the same volume of the reference image and same spatial coordinates; the map is initialized to a status of no tissue damage.

The operator identifies/defines using the tissue segmentation component (4) the target tissues, and optionally target margins (step 12).

The operator optionally segments the local vasculature and optionally identifies/defines perfusion regions and perfusion values (step 14).

The operator uses common image guidance procedures to deploy the ablation device (1) at a desired intracorporeal location which is in operator's experience suitable to perform a first ablation. The operator, before activating the ablation device (1), acquires a confirmation image, which captures the position and orientation of the ablation device (1), and informs, though a GUI, the adequacy evaluation component (6) that a confirmation image is available (step 18).

The adequacy evaluation component (6) uses the device identification component (5) to recognize the position and orientation of the ablation device (1), and optionally the geometry of the device as deployed in the tissues (step 20).

The adequacy evaluation component (6) uses device manufacturer data to estimate the ablation volume of the device. Optionally the adequacy evaluation component (6) can use computer models that simulate the physics of the ablation process, including the heat sink effect of the local vasculature, the effect of perfusion including the different perfusion rates for different tissues, and the actual geometry of the device as deployed in the tissues to estimate an ablation volume (step 22). FIG. 19 shows, as an example, a computational model, including an RFA electrode (1904), where a vessel (1901) is able absorb heat from an ablation site, as the temperature of blood is 37° C. and the temperature of the tissues at the ablation site exceeds 100° c. The presence of the vessels alters the temperature isolines, and shrinks the ablation volume, an effect known as "heat sink". Temperature isolines are represented as white stripes, where (1902) is the 60° C. isoline and (1903) the 100° C. isoline.

The adequacy evaluation component (6) will register the confirmation image to the reference image, allowing to refer the ablation device (1) position and orientation obtained from the device identification component (5) to the reference image. This will allow the adequacy evaluation component (6) to display, fused to the reference image, and to a representation of the target tissues, an estimated ablation volume The operator will assess the effects of the ablation, and in particular which portion of target tissues would be treated, and any possible damage to non-target tissues, from the visual representation of the ablation volume, of the reference image of the patient, and of the target tissues offered in a GUI by the adequacy evaluation component (6). If previous ablations have been run, because the operator has cycled on steps 40 to 16, the adequacy evaluation component (6) will also highlight which previous tissues have been treated, or which tissues are to be treated yet, or both (step 24).

If the position and orientation of the ablation device (1) are unsatisfactory the operator will re-position appropriately the ablation device (1) under image guidance and repeat steps 12 to 26 until the position and orientation of the ablation device (1) are satisfactory (step 26).

The operator, without moving the ablation device (1) from the position, which was deemed to be satisfactory at step 26, will inform, through a GUI, the adequacy evaluation component (6) that the ablation is being started, and the operator will start the ablation by operating the ablation device controller (2) (step 28).

The adequacy evaluation component (6) will optionally start a communication with the ablation device controller (2) (e.g. via a serial port, via a USB connection, via a Ethernet connection, via wireless means, or via any other means of machine-to-machine communication) for gathering information characterizing the ablation process, such as the level and duration of ablative power being applied to the tissues, or information characterizing the status of tissues like impedance data in RFA, the electromagnetic reflection coefficient data in MWA, or temperature data (step 30).

Figure 22:
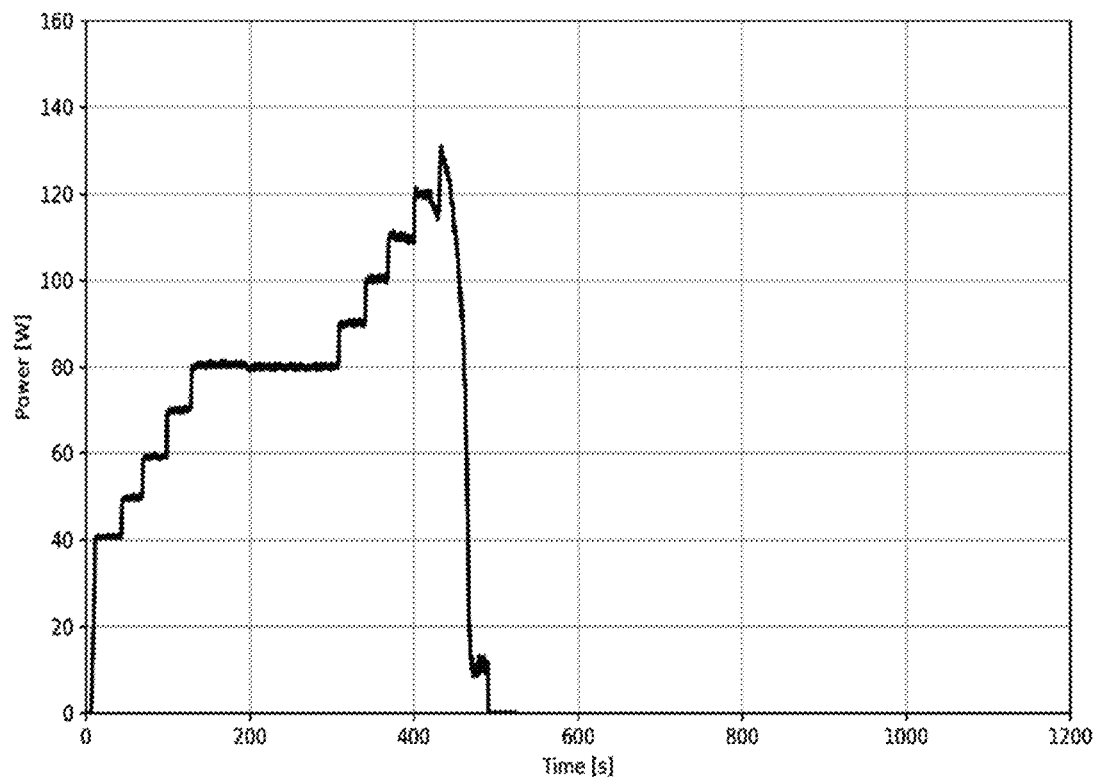
FIG. 22 depicts RF power information as collected from an RF power generator during an RF ablation.
Figure 23:
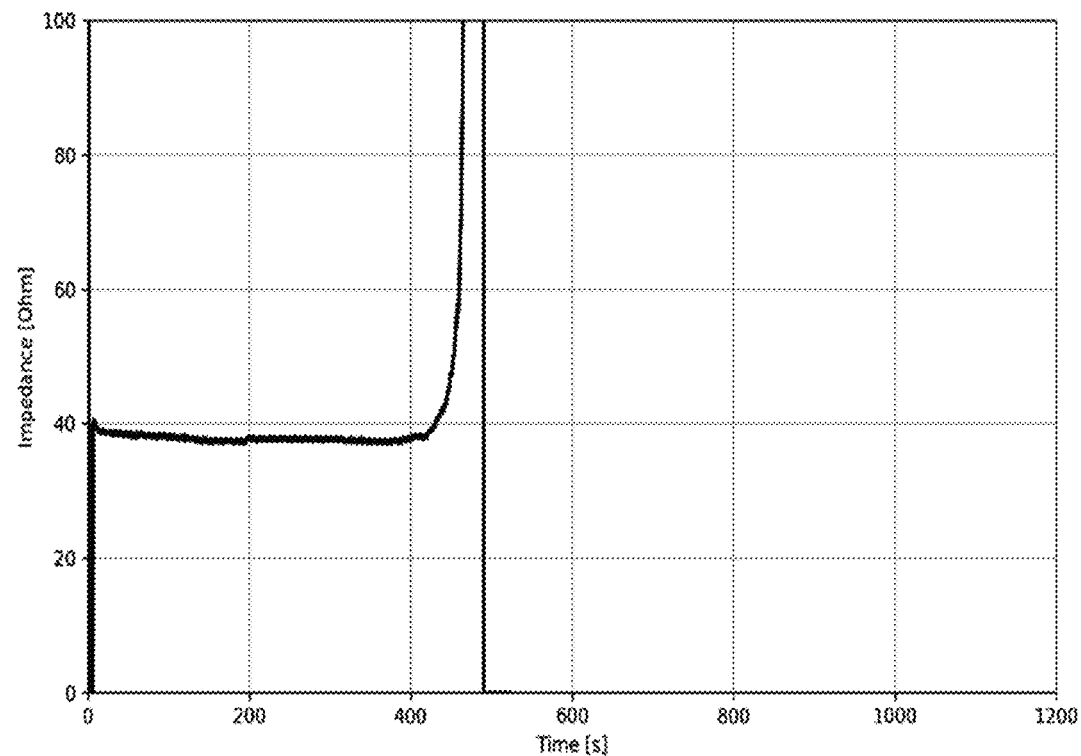
FIG. 23 depicts RF electrical impedance information as collected from an RF power generator during an RF ablation.

The data collected from the ablation device controller (2) during step 30 might be optionally used to update the estimated ablation volume, for example by using a computer model and re-computing the ablation volume based on the actual level of applied ablative power. FIG. 22 illustrates the temporal evolution of the applied power during an RFA ablation as collected by an RFA power generator (ablation device controller (2)). The power is varied over time by the operator according to a protocol specified by the manufacturer of the power generator and electrode. The actual delivered power depends, besides the variable settings of the operator, on the properties of the tissues, including the hydration state the perfusion rate. Retrieving data about the power applied from the ablation device controller (2), or other similar information that characterizes the ablation process in other forms of ablation, allows to run computer models based on this data and to obtain more accurate estimation of the ablation volume that has been procured in tissue. Ablation device controllers (2) optionally acquire data that characterizes the tissues. FIG. 23, for example, shows impedance data collected from an RFA power generator during the course of an ablation. Initially the impedance has a value of about 40 Ohms. Towards the end of the ablation the impedance raises quickly to more than 100 Ohms (and then decreases because the operator has switched off the power generator). The sharp increase in impedance reflects the fact that tissues have lost most of their water, which has evaporated under the intense heat of the ablation. Similar data, reflecting the status of tissues, can be used by computer models used to simulate ablation physics, to improve predictions in the estimate ablation volume. Models for thermal ablation for example estimate the water content of tissues during the ablation, and this data, or similar data can be used to estimate internal parameters of the model.

Upon termination of the ablation the operator informs the adequacy evaluation component (6), through a GUI, that the ablation has been terminated (step 34).

The adequacy evaluation component (6) uses the estimated ablation volume from step 22, or from step 32, if an update to the ablation volume was made, to mark treated tissues in the treated tissues map. The volume of tissues to be marked as treated is given from the ablation volume estimation steps 22 or 32. The spatial position and orientation of the estimated ablation volume are known form the device identification component (5) at step 20. This spatial information provided by the device identification component (5) is referred to the reference image and therefore to the treated tissues map, as the map by construction has the same system of spatial coordinates than the reference image.

The marking of tissues as treated is an accumulation process. If further ablations are performed, looping on steps 16 to 40, new tissues can be marked as treated, but a tissue that has been marked as treated cannot be unmarked.

Alternatively, when available, the adequacy evaluation component (6) might use further post-ablation images, registered to the reference image, to identify treated tissues and to mark them as treated in the treated tissues map.

The above operations complete step 36.

The treated tissues map, at this stage represents the volume of treated tissues from a first single ablation. If multiple ablations are performed looping on steps 16 to 40, the treated tissues map would have accumulated the volume of treated tissues for all the ablations that have been run.

The adequacy evaluation component (6) will display, using a GUI, the reference image defined in the tissue segmentation component (4), a representation of the target tissues, as defined in the tissue segmentation component (4), and representations that will allow the operator to estimate the adequacy. These representations, can, for example, highlight which target tissues have received treatment, or which target tissues still need treatment, or both, allowing a visual and straightforward evaluation of whether all target tissues have been treated, and therefore the evaluation of the adequacy of the procedure (step 38).

Figure 20:
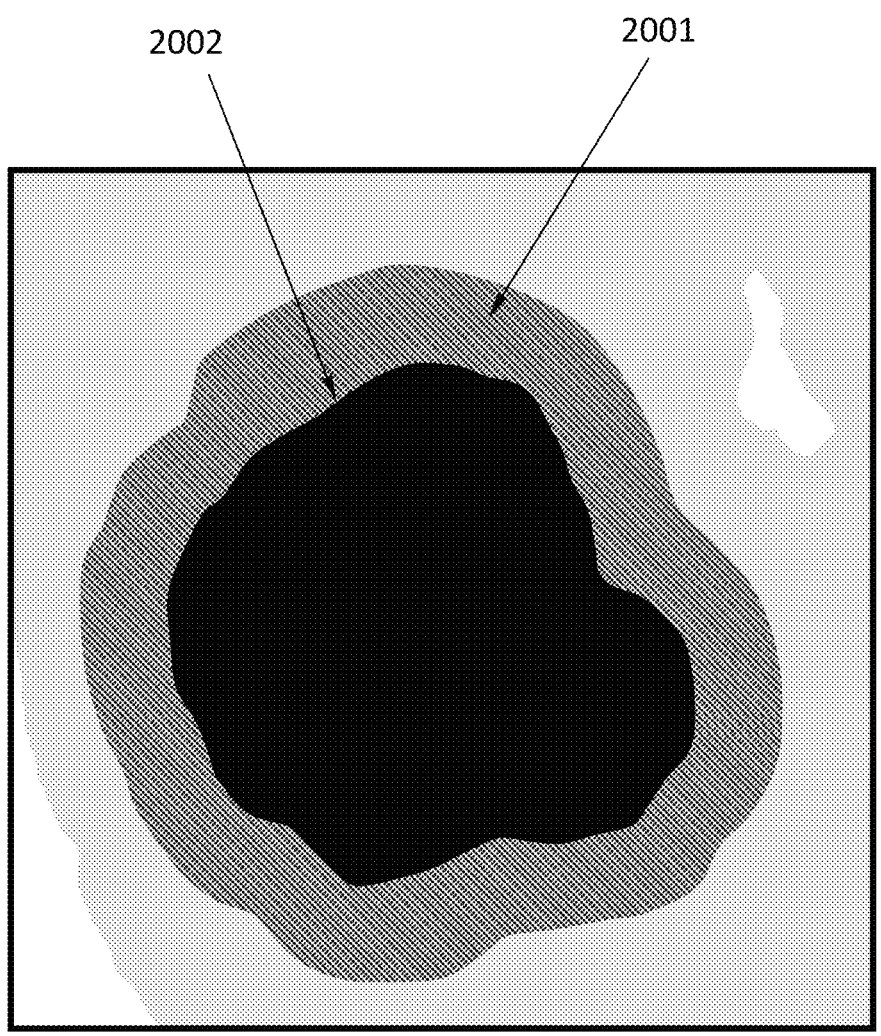
FIG. 20 depicts a CT slice and computer highlighted target tissues and margins.
Figure 21:
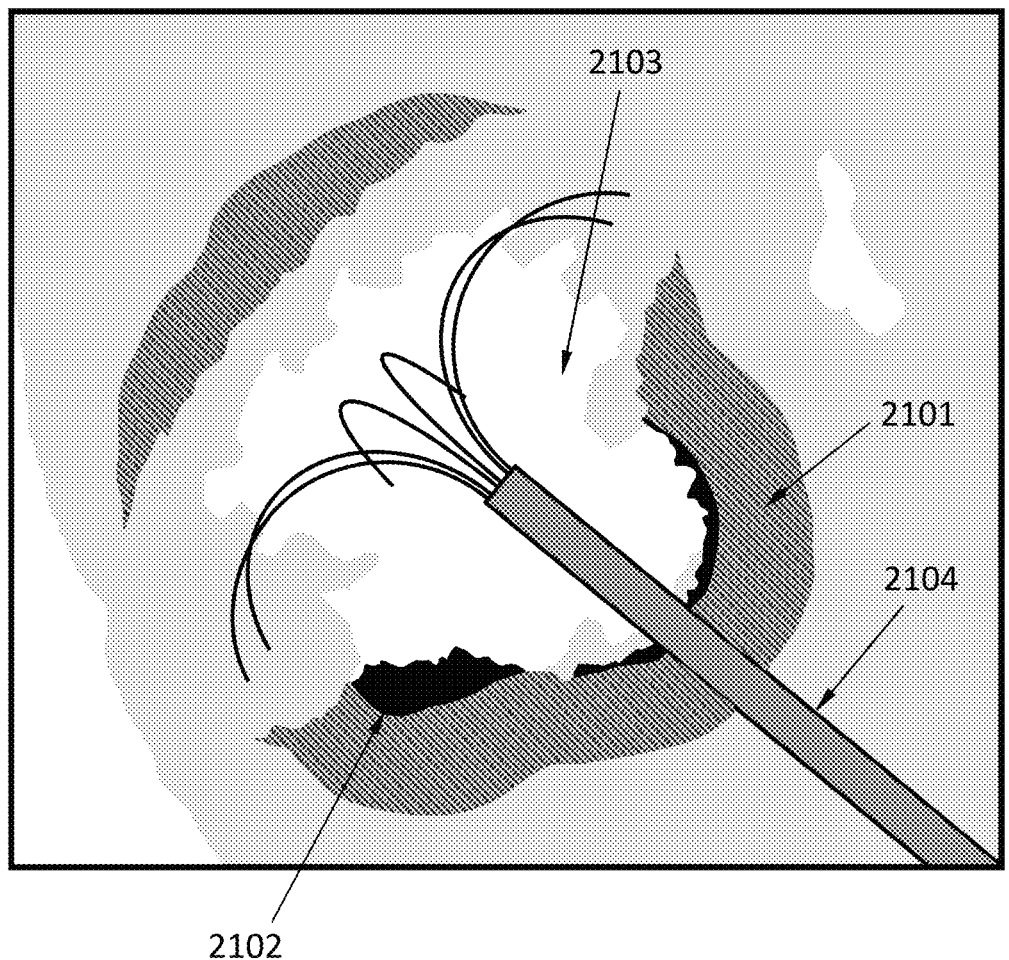
FIG. 21 depicts a CT slice with computer highlighted information that aids the evaluation of adequacy, namely a representation of target tissues and margins that still need treatment after a first ablation.

FIGS. 20 and 21 demonstrate the above step. FIG. 20 shows a 2D slice from the reference image, a segmented tumor (target tissues) and associated margins. The segmented tumor and margins are 3D volumes, of which a 2D slice in the same plane of the 2D slice of the reference image is represented. FIG. 21 shows a subtraction view, where the volume of treated tissues has been subtracted from the volume of the target tissue and margins. A 2D slice through these volumes and through the reference image is represented. The subtraction representation highlights therefore the tissues that still need treatment and makes the evaluation of adequacy a visual and straightforward task.

The above operations complete step 38.

If adequacy has been reached at step 40 the procedure is terminated.

If the adequacy has not been achieved the operator will loop through steps 16 to 40 until adequacy is reached.

Figure 24:
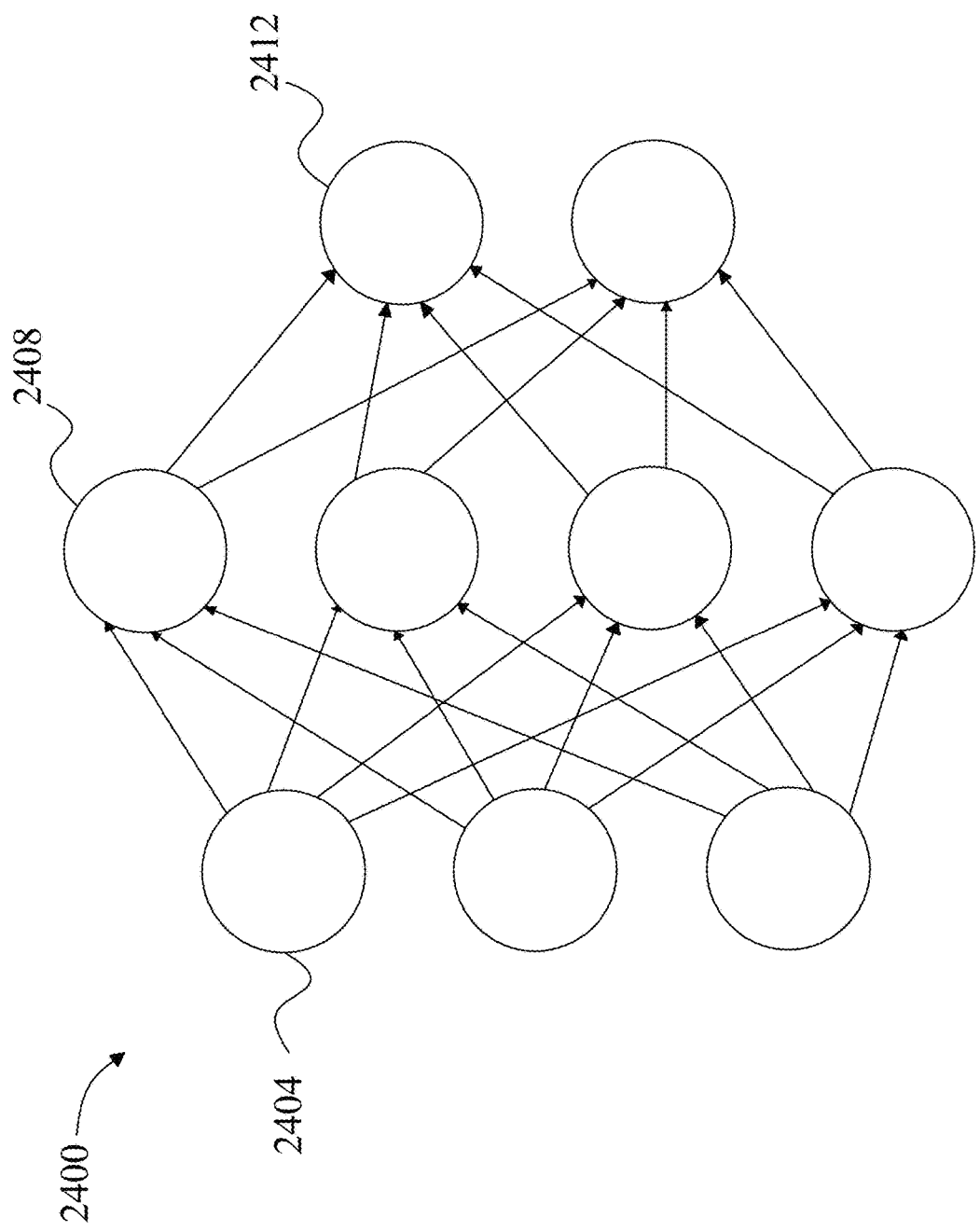
FIG. 24 depicts an exemplary embodiment of neural network.

Referring now to FIG. 24, an exemplary embodiment of neural network 2400 is illustrated. A neural network 2400 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 2404, one or more intermediate layers 2408, and an output layer of nodes 2412. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 25:
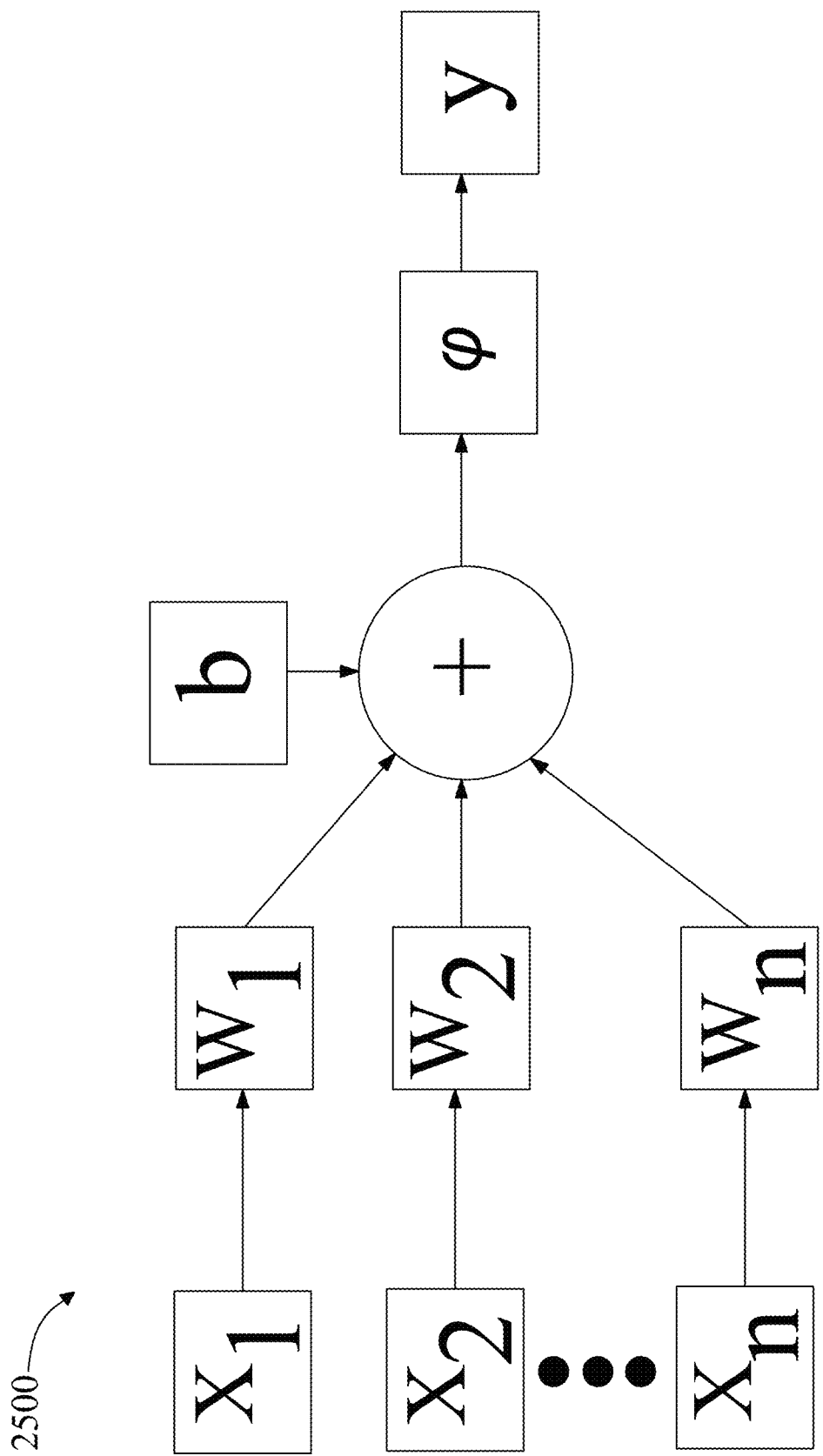
FIG. 25 depicts an exemplary embodiment of a node of a neural network.

Referring now to FIG. 25, an exemplary embodiment of a node of a neural network is illustrated. A node may include, without limitation a plurality of inputs $x_i$ that may receive numerical values from inputs to a neural network containing the node and/or from other nodes. Node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function $\varphi$, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 26:
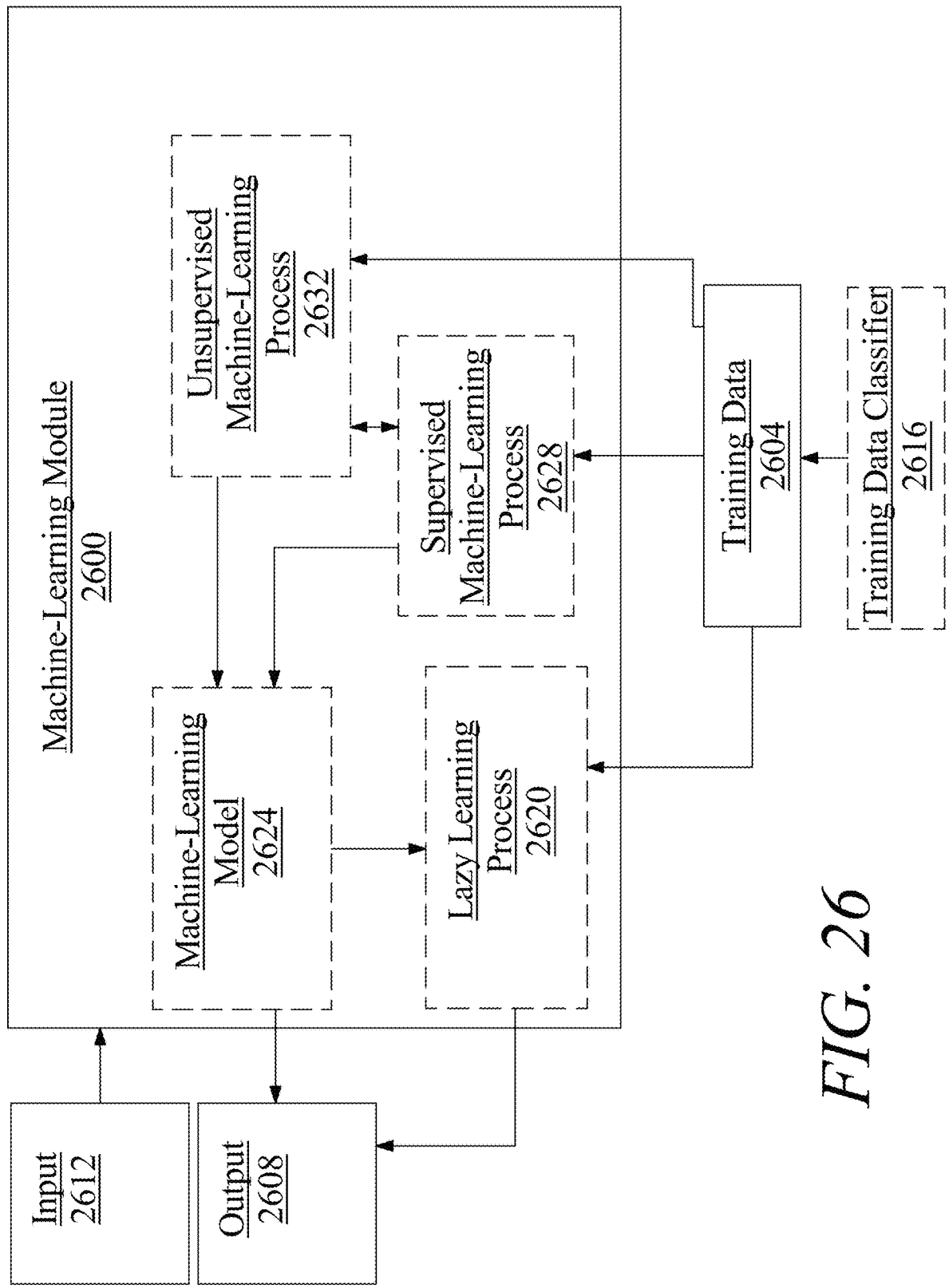
FIG. 26 is a box diagram of an exemplary embodiment of a machine learning module.

Referring now to FIG. 26, an exemplary embodiment of a machine-learning module 2600 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 2604 to generate an algorithm that will be performed by a computing device/module to produce outputs 2608 given data provided as inputs 2612; this is in contrast to a non-machine learning software program where the commands to be executed are determined in advance by a user and written in a programming language.

Still referring to FIG. 26, "training data," as used herein, is data containing correlations that a machine-learning process may use to model relationships between two or more categories of data elements. For instance, and without limitation, training data 2604 may include a plurality of data entries, each entry representing a set of data elements that were recorded, received, and/or generated together; data elements may be correlated by shared existence in a given data entry, by proximity in a given data entry, or the like. Multiple data entries in training data 2604 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 2604 according to various correlations; correlations may indicate causative and/or predictive links between categories of data elements, which may be modeled as relationships such as mathematical relationships by machine-learning processes as described in further detail below. Training data 2604 may be formatted and/or organized by categories of data elements, for instance by associating data elements with one or more descriptors corresponding to categories of data elements. As a non-limiting example, training data 2604 may include data entered in standardized forms by persons or processes, such that entry of a given data element in a given field in a form may be mapped to one or more descriptors of categories. Elements in training data 2604 may be linked to descriptors of categories by tags, tokens, or other data elements; for instance, and without limitation, training data 2604 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 26, training data 2604 may include one or more elements that are not categorized; that is, training data 2604 may not be formatted or contain descriptors for some elements of data. Machine-learning algorithms and/or other processes may sort training data 2604 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 2604 to be made applicable for two or more distinct machine-learning algorithms as described in further detail below. Training data 2604 used by machine-learning module 2600 may correlate any input data as described in this disclosure to any output data as described in this disclosure. As a non-limiting illustrative example inputs may include input images containing representations of a tissue ablation device as described above as inputs and outputs may include bounding boxes and class probabilities for detected objects.

Further referring to FIG. 26, training data may be filtered, sorted, and/or selected using one or more supervised and/or unsupervised machine-learning processes and/or models as described in further detail below; such models may include without limitation a training data classifier 2616. Training data classifier 2616 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 2600 may generate a classifier using a classification algorithm, defined as a process whereby a computing device and/or any module and/or component operating thereon derives a classifier from training data 2604. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 2616 may classify elements of training data to types of tissue ablation devices and/or tissue or types of tissue.

Still referring to FIG. 26, machine-learning module 2600 may be configured to perform a lazy-learning process 2620 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 2604. Heuristic may include selecting some number of highest-ranking associations and/or training data 2604 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 26, machine-learning processes as described in this disclosure may be used to generate machine-learning models 2624. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 2624 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 2624 may be generated by creating an artificial neural network, such as a convolutional neural network comprising an input layer of nodes, one or more intermediate layers, and an output layer of nodes. Connections between nodes may be created via the process of "training" the network, in which elements from a training data 2604 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 26, machine-learning algorithms may include at least a supervised machine-learning process 2628. At least a supervised machine-learning process 2628, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include input images containing representations of a tissue ablation device as described above as inputs, bounding boxes and class probabilities for detected objects as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 2604. Persons skilled in the art, upon reviewing the entirety of this disclosure, will be aware of various possible variations of at least a supervised machine-learning process 2628 that may be used to determine relation between inputs and outputs. Supervised machine-learning processes may include classification algorithms as defined above.

Further referring to FIG. 26, machine learning processes may include at least an unsupervised machine-learning processes 2632. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 26, machine-learning module 2600 may be designed and configured to create a machine-learning model 2624 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 26, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Figure 27:
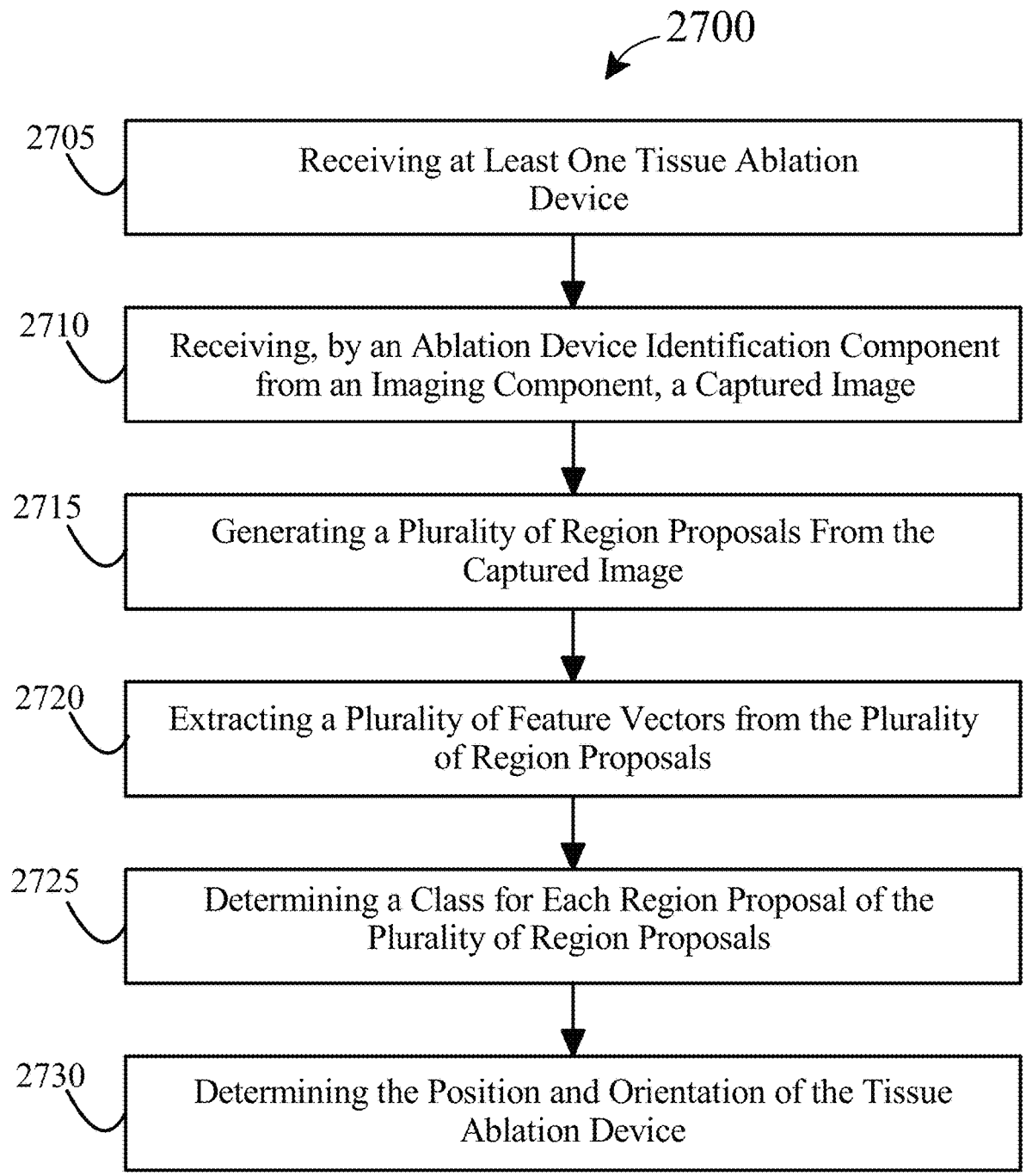
FIG. 27 is a flow diagram of an exemplary embodiment of a method for ablation treatment of tissues.

Referring now to FIG. 27, an exemplary embodiment of a method 2700 for ablation treatment of tissues is shown. Method 2700 includes a step 2705 of receiving at least one tissue ablation device, wherein the tissue ablation device is communicatively connected to an ablation device controller and configured to control the ablation effect of the at least one ablation device. This may be implemented, without limitation, as described above with reference to FIGS. 1-26. For example, tissue ablation device may be consistent with any tissue ablation device disclosed as part of this disclosure.

With continued reference to FIG. 27, method 2700 includes a step 2710 of receiving, by an ablation device identification component from an imaging component, a captured image, wherein the imaging component is configured to capture the captured image and the captured image comprises a representation of the tissue ablation device. This may be implemented, without limitation, as described above with reference to FIGS. 1-26.

With continued reference to FIG. 27, method 2700 may include the use of a neural network or convolutional neural network (CNN) as described above with respect to FIGS. 24 and 25. In some embodiments, the CNN may be a region-based convolutional neural network (R-CNN). An R-CNN may have a plurality of modules.

With continued reference to FIG. 27, the R-CNN may have a region extraction module. The region extraction module may extract a plurality of region proposals from an input image. As a non-limiting example, the region extraction module may be configured to extract a plurality of region proposals from the captured image that is captured in step 2710, as discussed above. In some embodiments, the region extraction module may be configured to extract 500 region proposals. In some embodiments, the region extraction module may be configured to extract 1,000 region proposals. In some embodiments, the region extraction module may be configured to extract 2,000 or more region proposals. Region proposals include portions of the input image. Region proposals may be generated using an algorithm. Region proposals may be generated using a selective search algorithm. A selective search algorithm generates region proposals by first over segmenting the input image. This may be done based on intensity of pixels using a graph-based segmentation method. For example, the graph-based segmentation method by Felzenszwalb and Huttenlocher. However, due to over segmentation, the objects in the input image may include more than one segment. The selective search algorithm may then group adjacent segments based on similarity to form the region proposals. This step of grouping adjacent segments may be performed iteratively. The selective search algorithm may group adjacent segments based on color similarity, texture similarity, size similarity, shape similarity, or a combination of the similarities. In some embodiments, another algorithm such as an EdgeBoxes algorithm may be used to generate the region proposal. The EdgeBoxes algorithm works on the assumption that the number of contours wholly enclosed by a bounding box is indicative of the likelihood of the box containing an object. It may be said that a contour is wholly enclosed by a box if all edge pixels belonging to the contour lie within the interior of the box. Thus, region proposals may be selected based on the number of contours that are wholly enclosed within the region proposal.

With continued reference to FIG. 27, as part of an R-CNN, in some embodiments, the plurality of region proposals may each be resized to a predetermined size. As a non-limiting example, the fixed predetermined size may be a 600×600 aspect ratio or 600×600 pixels. A person of ordinary skill in the art, after having reviewed the entirety of this disclosure, would appreciate that a variety of predetermined sizes may be chosen based on computational and practical needs.

With continued reference to FIG. 27, feature vectors may be extracted from each of the region proposals. For the purposes of this disclosure, a "feature vector" is an n-dimensional vector of numerical features. As a non-limiting example, the feature vector may include a histogram of oriented gradients (HOG). Ideally, a feature vector will adequately describe an object, regardless of whether the object varies due to a transformation, such as scaling or rotation. Each feature vector may be of a fixed pre-determined size. As a non-limiting example, each feature vector may be of a length 4,096. In the case of an R-CNN, as opposed to other object detection techniques, a CNN is used to extract the features from a region proposal. In an R-CNN, the extraction of features into feature vectors may be performed by a feature extraction module.

With continued reference to FIG. 27, the region proposal may be classified into a class as a function of the feature vector corresponding to that region proposal. In some embodiments, a Support Vector Machine (SVM) algorithm may be used to classify the region proposal into the classes. In some embodiments, as part of an R-CNN, an SVM algorithm may be used to classify the region proposal into the classes. In the SVM algorithm, each data item may be plotted as a point in n-dimensional space (where n is a number of features you have) with the value of each feature being the value of a particular coordinate. Then, classification may be performed by finding the hyper-plane that best separates the two classes.

With continued reference to FIG. 27, the classes may include a background class and one or more object classes. The one or more object classes may include classes for the one or more objects sought to be identified/detected. As a non-limiting example, in the case of an ablation probe, the object classes may include classes for the electrode, electrode shaft, tines, tissue, and the like. In some embodiments, ablation probe object classes may include classes for a shaft, tines, tissue, and the like. In some embodiments, this classification may be performed by a classification module in an R-CNN.

With continued reference to FIG. 27, in some embodiments, a Fast R-CNN may be used. A primary advantage of Fast R-CNN over normal R-CNN is its speed. Fast R-CNN uses a new layer called region of interest (ROI) pooling. Region of interest may also be referred to as a region proposal. Fast R-CNN may share computations, such as convolutional layer calculations, across all region proposals (ROIs) rather than doing the calculations for each region proposal independently. As a non-limiting example, if the region proposals are from the same input image, then the convolutional layers for those region proposals may be shared in Fast R-CNN. Fast R-CNN may use only one stage as opposed to the three stages (three modules) of the R-CNN discussed above. Fast R-CNN may receive an input image as input and output class probabilities and bounding boxes for the detected objects.

With continued reference to FIG. 27, in Fast R-CNN, the feature map from the last convolutional layer is fed into the ROI pooling layer, so that a fixed length feature vector may be extracted from each region proposal. The ROI pooling layer may divide each region proposal of the plurality of region proposals into a plurality of cells. The plurality of cells may be a grid. A max pooling operation may be applied to each cell in the plurality of cells to return a single value. The values from each of the cells may represent the feature vector. As a non-limiting example, if there is a 2×2 grid of cells, the feature vector length may be 4. In Fast R-CNN, the feature vector extracted using ROI pooling may be fed into fully connected layers. Fully connected layers are further discussed with reference to FIGS. 24 and 25. The output of the last fully connected layer may be split into two branches. One may be a Softmax layer used to predict class scores. The second may be a Fully connected layer to predict the bounding boxes of the detected objects.

With continued reference to FIG. 27, in some embodiments, a Faster R-CNN may be used. The primary improvement of Faster R-CNN over R-CNN is the use of a region proposal network (RPN). An RPN is a convolutional network that generates region proposals with various scales and aspect ratios. Additionally, convolutional calculations may be shared across the RPN and Fast R-CNN to further decrease computational time. Regarding the use of an RPN, because the proposals are generated using a network, the network can be trained end-to-end to be customized on the detection task. Thus, it produces better region proposals compared to generic methods like Selective Search and EdgeBoxes.

With continued reference to FIG. 27, the neural networks, such as R-CNN, discussed above may be trained using training data. Training data is discussed further with reference to FIG. 26. In some embodiments, training data may include training images, wherein the training images include a representation of a tissue ablation device. In some embodiments, the training images may also comprise imposter images comprising images of unrelated devices, or images that do not include a tissue ablation device. In some embodiments, the unrelated devices may be similar in shape to the tissue ablation device. The training images may be correlated to desired outputs such as bounding boxes and class probabilities for the training images. This training data, as non-limiting examples, may be used to train the classification module of R-CNN. As a non-limiting example, the training data may be used to train a Fast R-CNN. As a non-limiting example, the training data may be used to train an RPN, such as the RPN of a Faster R-CNN.

With continued reference to FIG. 27, method 2700 includes a step 2715 of generating, by the ablation device identification component, a plurality of region proposals from the captured image. This may be implemented, without limitation, as described above with reference to FIGS. 1-27. In some embodiments, step 2715 may include dividing each region proposal of the plurality of region proposals into a plurality of cells. This may be implemented, without limitation, as described above with reference to FIGS. 1-27.

With continued reference to FIG. 27, method 2700 includes a step 2720 of extracting, by the ablation device identification component, a plurality of feature vectors from the plurality of region proposals, wherein each feature vector of the plurality of feature vectors corresponds to a region proposal of the plurality of region proposals. This may be implemented, without limitation, as described above with reference to FIGS. 1-27.

With continued reference to FIG. 27, method 2700 includes a step 2725 of determining, by the ablation device identification component, a class for each region proposal of the plurality of region proposals, wherein determining the class for each region proposal is a function of the corresponding feature vector for the region proposal. This may be implemented, without limitation, as described above with reference to FIGS. 1-27. In some embodiments, the class may be chosen from a set of possible classes, wherein the set of possible classes comprises a background class and a plurality of object classes. This may be implemented, without limitation, as described above with reference to FIGS. 1-27. In some embodiments, step 2725 may be performed using a support vector machine algorithm. This may be implemented, without limitation, as described above with reference to FIGS. 1-27.

With continued reference to FIG. 27, method 2700 includes a step 2730 of determining the position and orientation of the tissue ablation device as a function of the classes for each region proposal. This may be implemented, without limitation, as described above with reference to FIGS. 1-27. In some embodiments, the bounding boxes and class probabilities used to calculate the position and orientation of the tissue ablation device, in accordance with the disclosure of FIGS. 1-23. In some embodiments, step 2730 may include determining the position of the proximal end and the distal end. This may be implemented, without limitation, as described above with reference to FIGS. 1-27. In some embodiments, determining the position of the proximal end and the distal end may include determining a proximal end keypoint corresponding to the proximal end. This may be implemented, without limitation, as described above with reference to FIGS. 1-27. In some embodiments, determining the position of the proximal end and the distal end may include determining a distal end keypoint corresponding to the distal end. This may be implemented, without limitation, as described above with reference to FIGS. 1-27. In some embodiments, step 2700 may include determining the position of the at least an intermediary point. This may be implemented, without limitation, as described above with reference to FIGS. 1-27. In some embodiments, determining the position of the at least an intermediary point may include determining an intermediary point keypoint associated with the intermediary point. This may be implemented, without limitation, as described above with reference to FIGS. 1-27. In some embodiments, step 2700 may include determining the position of the attachment point, the free end, and the tine intermediary point. This may be implemented, without limitation, as described above with reference to FIGS. 1-27. In some embodiments, determining the position of the attachment point, the free end, and the tine intermediary point may include determining an attachment point keypoint associated with the attachment point. This may be implemented, without limitation, as described above with reference to FIGS. 1-27. In some embodiments, determining the position of the attachment point, the free end, and the tine intermediary point may include determining a free end keypoint associated with the free end. This may be implemented, without limitation, as described above with reference to FIGS. 1-27. In some embodiments, determining the position of the attachment point, the free end, and the tine intermediary point may include determining a tine intermediary point keypoint associated with the tine intermediary point. This may be implemented, without limitation, as described above with reference to FIGS. 1-27.

With continued reference to FIG. 27, in some embodiments, method 2700 may further include a step of resizing each region proposal of the plurality of region proposals to a predefined size. This may be implemented, without limitation, as described above with reference to FIGS. 1-27.

It is to be noted that any one or more of the aspects and embodiments described herein may be conveniently implemented using one or more machines (e.g., one or more computing devices that are utilized as a user computing device for processing images, processing medical images, an electronic document, one or more server devices, such as an image processing sever, a document server) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 28:
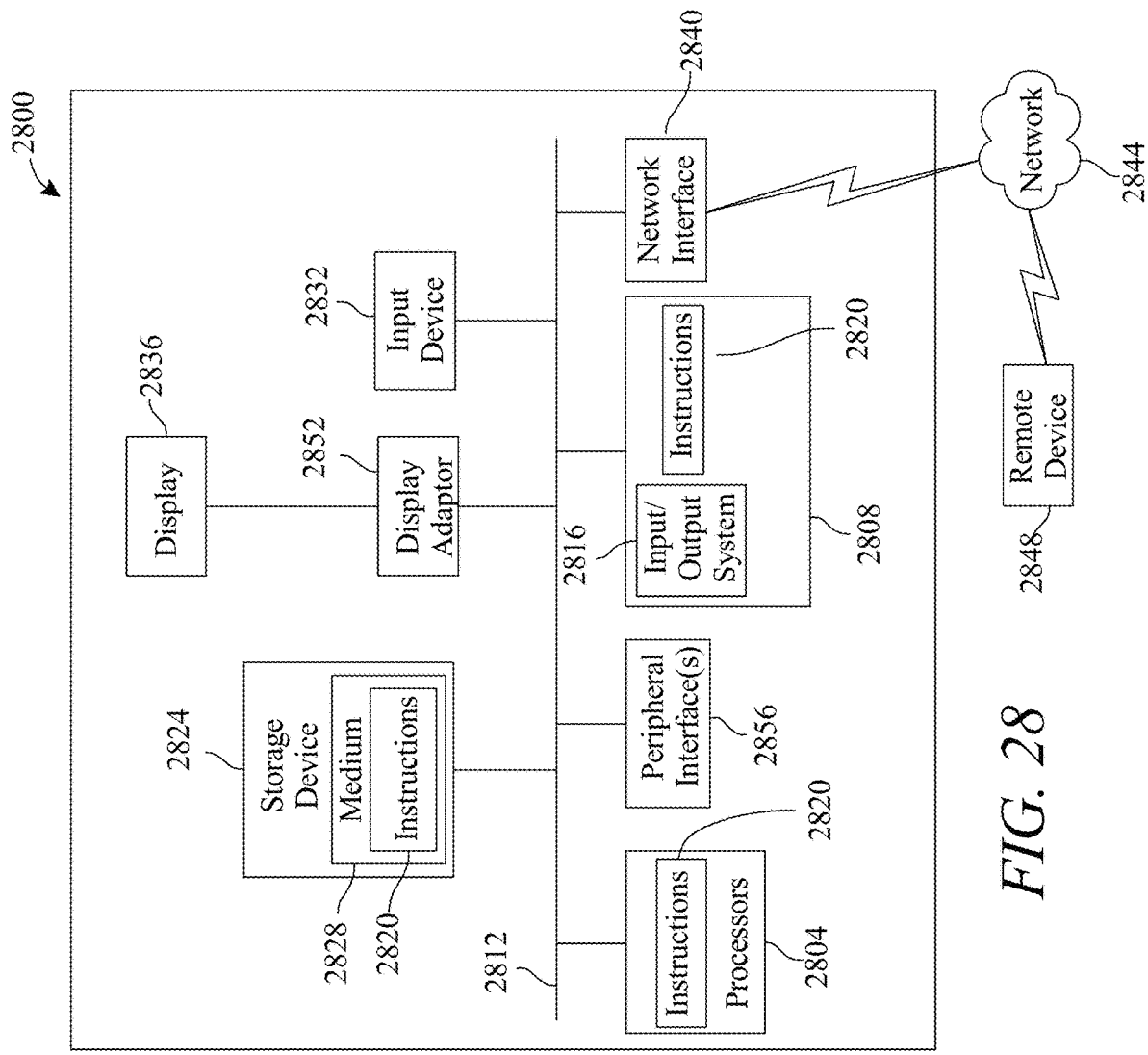
FIG. 28 is a block diagram of a computing system that can be used to implement any one or more of the methodologies disclosed herein and any one or more portions thereof.

FIG. 28 shows a diagrammatic representation of one embodiment of a computing device in the exemplary form of a computer system 2800 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 2800 includes a processor 2804 and a memory 2808 that communicate with each other, and with other components, via a bus 2812. Bus 2812 may include any of several types of bus structures including, but not limited to, a memory bus, a memory controller, a peripheral bus, a local bus, and any combinations thereof, using any of a variety of bus architectures.

Processor 2804 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 2804 may be organized according to Von Neumann and/or Harvard architecture as a non-limiting example. Processor 2804 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 2808 may include various components (e.g., machine-readable media) including, but not limited to, a random-access memory component, a read only component, and any combinations thereof. In one example, a basic input/output system 2816 (BIOS), including basic routines that help to transfer information between elements within computer system 2800, such as during start-up, may be stored in memory 2808. Memory 2808 may also include (e.g., stored on one or more machine-readable media) instructions (e.g., software) 2820 embodying any one or more of the aspects and/or methodologies of the present disclosure. In another example, memory 2808 may further include any number of program modules including, but not limited to, an operating system, one or more application programs, other program modules, program data, and any combinations thereof.

Computer system 2800 may also include a storage device 2824. Examples of a storage device (e.g., storage device 2824) include, but are not limited to, a hard disk drive, a magnetic disk drive, an optical disc drive in combination with an optical medium, a solid-state memory device, and any combinations thereof. Storage device 2824 may be connected to bus 2812 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 2824 (or one or more components thereof) may be removably interfaced with computer system 2800 (e.g., via an external port connector (not shown)). Particularly, storage device 2824 and an associated machine-readable medium 2828 may provide nonvolatile and/or volatile storage of machine-readable instructions, data structures, program modules, and/or other data for computer system 2800. In one example, software 2820 may reside, completely or partially, within machine-readable medium 2828. In another example, software 2820 may reside, completely or partially, within processor 2804.

Computer system 2800 may also include an input device 2832. In one example, a user of computer system 2800 may enter commands and/or other information into computer system 2800 via input device 2832. Examples of an input device 2832 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 2832 may be interfaced to bus 2812 via any of a variety of interfaces (not shown) including, but not limited to, a serial interface, a parallel interface, a game port, a USB interface, a FIREWIRE interface, a direct interface to bus 2812, and any combinations thereof. Input device 2832 may include a touch screen interface that may be a part of or separate from display 2836, discussed further below. Input device 2832 may be utilized as a user selection device for selecting one or more graphical representations in a graphical interface as described above.

A user may also input commands and/or other information to computer system 2800 via storage device 2824 (e.g., a removable disk drive, a flash drive, etc.) and/or network interface device 2840. A network interface device, such as network interface device 2840, may be utilized for connecting computer system 2800 to one or more of a variety of networks, such as network 2844, and one or more remote devices 2848 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 2844, may employ a wired and/or a wireless mode of communication. In general, any network topology may be used. Information (e.g., data, software 2820, etc.) may be communicated to and/or from computer system 2800 via network interface device 2840.

Computer system 2800 may further include a video display adapter 2852 for communicating a displayable image to a display device, such as display device 2836. Examples of a display device include, but are not limited to, a liquid crystal display (LCD), a cathode ray tube (CRT), a plasma display, a light emitting diode (LED) display, and any combinations thereof. Display adapter 2852 and display device 2836 may be utilized in combination with processor 2804 to provide graphical representations of aspects of the present disclosure. In addition to a display device, computer system 2800 may include one or more other peripheral output devices including, but not limited to, an audio speaker, a printer, and any combinations thereof. Such peripheral output devices may be connected to bus 2812 via a peripheral interface 2856. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods and systems according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for ablation of tissues, the system comprising:
   a tissue ablation device configured to produce an ablation effect to ablate tissue;
   an ablation device controller communicatively connected to the tissue ablation device, wherein the ablation device controller is configured to control the ablation effect of the ablation device by supplying at least one of an adjustment of energy and a temperature to the ablation device;
   an imaging component for capturing one or more images of tissues designated for treatment using the at least one ablation device, wherein:

the imaging component comprises one selected from the group consisting of a CT scanner, an US scanner, an MRI scanner, and a FL system; and the imaging component is configured to capture a reference image showing the target tissue to be ablated, and at least one confirmation image showing the tissue ablation device disposed proximate the tissue to be ablated; and an ablation device identification component, wherein the ablation device identification component is configured to:

use an automatic image processing algorithm to determine the position and orientation of the ablation device within the confirmation image; and an adequacy evaluation component comprising a display, the adequacy evaluation component being configured to:

(i) determine the location and volume of tissue ablated by the ablation device;

(ii) generate an evaluation image by displaying a visual representation of the volume of tissue ablated by the ablation effect of the ablation device superimposed on the reference image; and (iii) display the evaluation image on the display;

wherein the tissue ablation device further comprises a shaft, the shaft comprising a first end and a second end; and wherein determining the position and orientation of the tissue ablation device comprises:

assigning a first end keypoint to the first end of the shaft; and assigning a second end keypoint to the second end of the shaft; and passing a line through the first end keypoint and the second end keypoint, the line being representative of the shaft of the tissue ablation device.

2. The system of claim 1, wherein the evaluation image further comprises a visual representation of target tissue that has not been ablated by the ablation effect of the ablation device.

3. The system of claim 1, wherein:

the shaft further comprises at least one intermediary point, wherein the at least one intermediary point is located on the shaft between the first end and the second end; and wherein determining the position and orientation of the tissue ablation device further comprises determining the position of the at least one intermediary point.

4. The system of claim 1, wherein the tissue ablation device further comprises a plurality of tines, and further wherein:

each tine of the plurality of tines comprises:

an attachment point where the tine of the plurality of tines attaches to the shaft;

a free end, wherein the free end is at an opposite end of the tine of the plurality of tines from the attachment point; and at least one tine intermediary point, wherein the at least one tine intermediary point is located on the tine of the plurality of tines between the attachment point and the free end; and each tine of the plurality of tines is attached to the shaft; and wherein determining the position and orientation of the tissue ablation device comprises determining the position of the attachment point, the free end, and the at least one tine intermediary point.

5. The system of claim 4, wherein the plurality of tines are attached to the shaft so as to extend radially from the shaft.

6. The system of claim 4, wherein determining the position of the attachment point, the free end, and the at least one tine intermediary point comprises:

determining an attachment point keypoint associated with the attachment point;

determining a free end keypoint associated with the free end;

determining at least one tine intermediary point keypoint associated with the at least one tine intermediary point; and passing a line through the attachment point keypoint, the at least one tine intermediary point keypoint, and the free end keypoint.

7. A method for ablating tissue, the method comprising:

providing a system for ablation of tissues, the system comprising:

a tissue ablation device configured to produce an ablation effect to ablate tissue;

an ablation device controller communicatively connected to the tissue ablation device, wherein the ablation device controller is configured to control the ablation effect of the ablation device by supplying at least one of an adjustment of energy and a temperature to the ablation device;

an imaging component for capturing one or more images of tissues designated for treatment using the at least one ablation device, wherein:

the imaging component comprises one selected from the group consisting of a CT scanner, an US scanner, an MRI scanner, and a FL system; and the imaging component is configured to capture a reference image showing the target tissue to be ablated, and at least one confirmation image showing the tissue ablation device disposed proximate the tissue to be ablated; and an ablation device identification component, wherein the ablation device identification component is configured to:

use an automatic image processing algorithm to determine the position and orientation of the ablation device within the confirmation image; and an adequacy evaluation component comprising a display, the adequacy evaluation component being configured to:

(i) determine the location and volume of tissue ablated by the ablation device;

(ii) generate an evaluation image by displaying a visual representation of the volume of tissue ablated by the ablation effect of the ablation device superimposed on the reference image; and (iii) display the evaluation image on the display;

imaging the target tissue that is to be ablated so as to generate the reference image;

wherein the tissue ablation device further comprises a shaft, the shaft comprising a first end and a second end; and wherein determining the position and orientation of the tissue ablation device comprises:

assigning a first end keypoint to the first end of the shaft; and assigning a second end keypoint to the second end of the shaft; and passing a line through the first end keypoint and the second end keypoint, the line being representative of the shaft of the tissue ablation device;

imaging the ablation device disposed proximate the target tissue so as to generate at least one confirmation image showing the ablation device in registration with the reference image, wherein the ablation device identification component is configured to identify the tissue ablation device on the reference image;

actuating the tissue ablation device using the ablation device controller so as to produce the ablation effect and ablate tissue proximate the tissue ablation device;

determining the volume of tissue ablated by the ablation device using the adequacy evaluation component;

generating an evaluation image using the adequacy evaluation component, wherein the evaluation image comprises displaying a visual representation of the volume of tissue ablated by the ablation effect of the ablation device on the reference image superimposed over the target tissue; and displaying the evaluation image on the display.

8. The method of claim 7, wherein the evaluation image further comprises a visual representation of target tissue that has not been ablated by the ablation effect of the ablation device.

9. The method of claim 7, wherein:
the shaft of the tissue ablation device further comprises at least one intermediary point, wherein the at least one intermediary point is located on the shaft between the first end and the second end; and
wherein determining the position and orientation of the tissue ablation device further comprises determining the position of the at least one intermediary point.

10. The method of claim 7, wherein the tissue ablation device further comprises a plurality of tines, and further wherein:
each tine of the plurality of tines comprises:
an attachment point where the tine of the plurality of tines attaches to the shaft of the tissue ablation device;
a free end, wherein the free end is at an opposite end of the tine of the plurality of tines from the attachment point; and
at least one tine intermediary point, wherein the at least one tine intermediary point is located on the tine of the plurality of tines between the attachment point and the free end; and
each tine of the plurality of tines is attached to the shaft of the tissue ablation device; and
wherein determining the position and orientation of the tissue ablation device comprises determining the position of the attachment point, the free end, and the at least one tine intermediary point.

11. The method of claim 10, wherein the plurality of tines are attached to the shaft of the tissue ablation device so as to extend radially from the shaft.

12. The method of claim 10, wherein determining the position of the attachment point, the free end, and the at least one tine intermediary point comprises:
determining an attachment point keypoint associated with the attachment point;
determining a free end keypoint associated with the free end;
determining at least one tine intermediary point keypoint associated with the at least one tine intermediary point; and
passing a line through the attachment point keypoint, the at least one tine intermediary point keypoint, and the free end keypoint.

13. A system for ablation of tissues, the system comprising:
a tissue ablation device configured to produce an ablation effect to ablate tissue;
an ablation device controller communicatively connected to the tissue ablation device, wherein the ablation device controller is configured to control the ablation effect of the ablation device by supplying at least one of an adjustment of energy and a temperature to the ablation device;
an imaging component for capturing one or more images of tissues designated for treatment using the at least one ablation device, wherein:
the imaging component comprises one selected from the group consisting of a CT scanner, an US scanner, an MRI scanner, and a FL system; and
the imaging component is configured to capture a reference image showing the target tissue to be ablated, and at least one confirmation image showing the tissue ablation device disposed proximate the tissue to be ablated; and
an ablation device identification component, wherein the ablation device identification component is configured to:
use an automatic image processing algorithm to determine the position and orientation of the ablation device within the confirmation image; and
an adequacy evaluation component comprising a display, the adequacy evaluation component being configured to:
(i) determine the location and volume of tissue ablated by the ablation device;
(ii) generate an evaluation image by displaying a visual representation of the volume of tissue ablated by the ablation effect of the ablation device superimposed on the reference image; and
(iii) display the evaluation image on the display;
wherein the tissue ablation device further comprises a shaft, the shaft comprising a first end and a second end; and
wherein the tissue ablation device further comprises a plurality of tines, and further wherein:
each tine of the plurality of tines comprises:
an attachment point where the tine of the plurality of tines attaches to the shaft;
a free end, wherein the free end is at an opposite end of the tine of the plurality of tines from the attachment point; and
at least one tine intermediary point, wherein the at least one tine intermediary point is located on the tine of the plurality of tines between the attachment point and the free end; and
each tine of the plurality of tines is attached to the shaft; and
wherein determining the position and orientation of the tissue ablation device comprises determining the position of the attachment point, the free end, and the at least one tine intermediary point.

14. A method for ablating tissue, the method comprising:
providing a system for ablation of tissues, the system comprising:
a tissue ablation device configured to produce an ablation effect to ablate tissue;
an ablation device controller communicatively connected to the tissue ablation device, wherein the ablation device controller is configured to control the ablation effect of the ablation device by supplying at least one of an adjustment of energy and a temperature to the ablation device;
an imaging component for capturing one or more images of tissues designated for treatment using the at least one ablation device, wherein:
  the imaging component comprises one selected from the group consisting of a CT scanner, an US scanner, an MRI scanner, and a FL system; and
  the imaging component is configured to capture a reference image showing the target tissue to be ablated, and at least one confirmation image showing the tissue ablation device disposed proximate the tissue to be ablated; and
an ablation device identification component, wherein the ablation device identification component is configured to:
  use an automatic image processing algorithm to determine the position and orientation of the ablation device within the confirmation image; and
an adequacy evaluation component comprising a display, the adequacy evaluation component being configured to:
  (i) determine the location and volume of tissue ablated by the ablation device;
  (ii) generate an evaluation image by displaying a visual representation of the volume of tissue ablated by the ablation effect of the ablation device superimposed on the reference image; and
  (iii) display the evaluation image on the display;
imaging the target tissue that is to be ablated so as to generate the reference image;
wherein the tissue ablation device further comprises a shaft, the shaft comprising a first end and a second end; and
wherein the tissue ablation device further comprises a plurality of tines, and further wherein:
  each tine of the plurality of tines comprises:
    an attachment point where the tine of the plurality of tines attaches to the shaft of the tissue ablation device;
    a free end, wherein the free end is at an opposite end of the tine of the plurality of tines from the attachment point; and
    at least one tine intermediary point, wherein the at least one tine intermediary point is located on the tine of the plurality of tines between the attachment point and the free end; and
  each tine of the plurality of tines is attached to the shaft of the tissue ablation device; and
  wherein determining the position and orientation of the tissue ablation device comprises determining the position of the attachment point, the free end, and the at least one tine intermediary point;
imaging the ablation device disposed proximate the target tissue so as to generate at least one confirmation image showing the ablation device in registration with the reference image, wherein the ablation device identification component is configured to identify the tissue ablation device on the reference image;
actuating the tissue ablation device using the ablation device controller so as to produce the ablation effect and ablate tissue proximate the tissue ablation device;
determining the volume of tissue ablated by the ablation device using the adequacy evaluation component;
generating an evaluation image using the adequacy evaluation component, wherein the evaluation image comprises displaying a visual representation of the volume of tissue ablated by the ablation effect of the ablation device on the reference image superimposed over the target tissue; and
displaying the evaluation image on the display.

* * * * *